United States Patent [19]

Breuer et al.

[11] 4,097,670
[45] * Jun. 27, 1978

[54] CARBOXYALKYLUREIDO CEPHALOSPORINS

[75] Inventors: Hermann Breuer; Uwe D. Treuner, both of Regensburg, Germany

[73] Assignee: E. R. Squibb & Sons, Inc., Princeton, N.J.

[*] Notice: The portion of the term of this patent subsequent to Apr. 25, 1995, has been disclaimed.

[21] Appl. No.: 673,222

[22] Filed: Apr. 5, 1976

[51] Int. Cl.² ........................................... C07D 501/36
[52] U.S. Cl. .............................. 544/27; 260/332.2 A;
560/34; 560/123; 424/246; 544/21; 544/26;
544/23; 560/124; 560/125; 560/122; 560/142;
560/155; 560/145; 560/173 L; 560/17;
560/170; 560/129
[58] Field of Search ................................. 260/243 C

[56] References Cited

U.S. PATENT DOCUMENTS

| | | | |
|---|---|---|---|
| 3,708,479 | 1/1973 | Welch et al. | 260/243 C |
| 3,925,368 | 12/1975 | Cooper et al. | 260/243 C |
| 3,932,392 | 1/1976 | Johnson et al. | 260/243 C |
| 3,935,204 | 1/1976 | Dahlen et al. | 260/243 C |

*Primary Examiner*—Nicholas S. Rizzo
*Assistant Examiner*—David E. Wheeler
*Attorney, Agent, or Firm*—Lawrence S. Levinson; Merle J. Smith; Stephen B. Davis

[57] ABSTRACT

Carboxyalkylureido cephalosporins of the formula

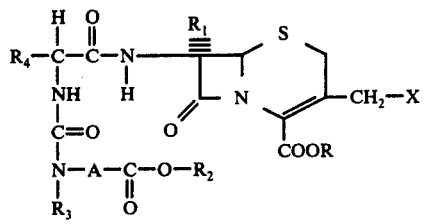

wherein R is hydrogen, lower alkyl, phenyl-lower alkyl, diphenyl-lower alkyl, tri(lower alkyl)silyl, trihaloethyl, a salt forming ion, or the group

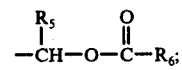

$R_1$ is hydrogen or methoxy; A is straight or branched chain alkylene of 1 to 6 carbons; $R_2$ is hydrogen, lower alkyl, phenyl, phenyl-lower alkyl, diphenyl-lower alkyl, alkali metal ion or alkaline earth metal ion; $R_3$ is hydrogen or lower alkyl; $R_4$ is hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups; $R_5$ is hydrogen or lower alkyl; $R_6$ is lower alkyl; and X is hydrogen, lower alkanoyloxy,

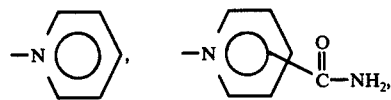

or certain heterothio groups; are disclosed. These compounds are useful as antibacterial agents.

32 Claims, No Drawings

CARBOXYALKYLUREIDO CEPHALOSPORINS

BACKGROUND OF THE INVENTION

Cephalosporins having a ureido acyl side chain are disclosed in U.S. Pat. Nos. 3,673,183; 3,708,479; 3,833,568; and 3,860,591. Cephalosporins having various acyl side chains and a 7α-methoxy substituent are taught in various U.S. patents including 3,775,410; 3,780,031; 3,780,033; 3,780,034; 3,780,037; 3,843,641; etc.

Cephalosporins having an acylureido acyl side chain are disclosed in U.S. Pat. Nos. 3,687,949 and 3,925,368 and German Offenlegungsschrift Nos. 2,513,954 and 2,514,019.

SUMMARY OF THE INVENTION

This invention relates to new carboxyalkylureido-7α-methoxy or desmethoxy cephalosporin derivatives of the formula $$\begin{array}{c} H \quad O \quad R_1 \\ R_4-\overset{|}{\underset{|}{C^*}}-\overset{\|}{C}-\overset{|}{\underset{H}{N}}\equiv\begin{array}{c}S\\ \\ N\end{array}\begin{array}{c}\\ \\ CH_2-X\end{array}\\ NH \\ \overset{|}{C}=O \quad O \quad COOR \\ \overset{|}{N}-A-\overset{\|}{\underset{O}{C}}-O-R_2 \\ \overset{|}{R_3} \end{array} \quad (I)$$

R represents hydrogen, lower alkyl, phenyl-lower alkyl, diphenyl-lower alkyl, tri(lower alkyl)silyl, trihaloethyl, a salt forming ion, or the group $$\begin{array}{c} R_5 \quad O \\ | \quad \| \\ -CH-O-C-R_6 \end{array}$$

wherein $R_5$ is hydrogen or lower alkyl and $R_6$ is lower alkyl.

$R_1$ represents hydrogen or methoxy. The $R_1$ substituent is in the α-configuration as indicated by the broken lines ($\equiv$).

A represents straight or branched chain alkylene of 1 to 6 carbons.

$R_2$ represents hydrogen, lower alkyl, phenyl, phenyl-lower alkyl, diphenyl-lower alkyl, alkali metal ion, or alkaline earth metal ion.

$R_3$ represents hydrogen or lower alkyl.

$R_4$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

X represents hydrogen, lower alkanoyloxy, certain heterothio groups, $$-N\bigcirc, \text{ or } -N\bigcirc\overset{O}{\underset{\|}{C}}-NH_2.$$

When X is pyridinium or carbamoyl substituted pyridinium, the compounds can be structurally represented as having the formula $$\begin{array}{c} H \quad O \quad R_1 \\ R_4-\overset{|}{\underset{|}{C^*}}-\overset{\|}{C}-\overset{|}{\underset{H}{N}}\equiv\begin{array}{c}S\\ \\ N\end{array}\begin{array}{c}\\ \\ CH_2-\overset{\oplus}{N}\bigcirc Z\end{array}\\ NH \\ \overset{|}{C}=O \quad O \quad COO^{\ominus} \\ \overset{|}{N}-A-\overset{\|}{\underset{O}{C}}-O-R_2 \\ \overset{|}{R_3} \end{array} \quad (Ia)$$

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, preferably benzyl, phenethyl, and diphenylmethyl.

Cycloalkyl refers to groups having 3 to 7 carbons in the ring, i.e. cyclopropyl, cyclobutyl, cyclopentyl, cyclohexyl, and cycloheptyl. The term cycloalkenyl also represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups include one or two substituents selected from halogen (preferably chorine or bromine), lower alkyl of 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4-methylphenyl, 2-, 3-, or 4-ethoxyphenyl, etc.

Straight or branch chain alkylene of 1 to 6 carbons is intended to include groups such as —$(CH_2)_n$— wherein $n$ is an integer from 1 to 6, $$-CH-,\ \begin{array}{c}CH_3\\|\\-C-\\|\\CH_3\end{array},\ -CH_2-CH-,\ -CH_2-CH-CH_2-,$$
$$\begin{array}{c}|\\CH_3\end{array}\quad\quad\quad\quad\begin{array}{c}|\\CH_3\end{array}\quad\quad\begin{array}{c}|\\CH_3\end{array}$$
$$-CH_2-CH-(CH_2)_2-,\ \text{etc.}$$
$$\begin{array}{c}|\\CH_3\end{array}$$

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

Also, the alkali metal and alkaline earth metal ions represented by $R_2$ are sodium, potassium, calcium and magnesium of which sodium and potassium are preferred.

The halogens are the four common halogens, of which chlorine and bromine are preferred. In the case of the trihaloethyl group represented by R,2,2,2-trichloroethyl is preferred.

Trimethylsilyl is the preferred tri(lower alkyl)silyl group.

The heterocyclic groups represented by $R_4$ are 2-thienyl, 3-thienyl, 2-furyl, 3-furyl, 2-pyridyl, 3-pyridyl, or 4-pyridyl. Also included within the meaning of $R_4$ are such heterocyclics having a halogen (preferably Cl or Br) or a lower alkyl of 1-4 carbons (preferably methyl or ethyl) substituent, i.e. 2-(4-chlorothienyl), 3-(4-methylthienyl), etc.

Lower alkanoyloxy refers to a group of the formula

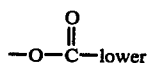

alkyl wherein lower alkyl is of 1 to 4 carbons, preferably wherein lower alkyl is methyl.

The heterothio groups represented by X are

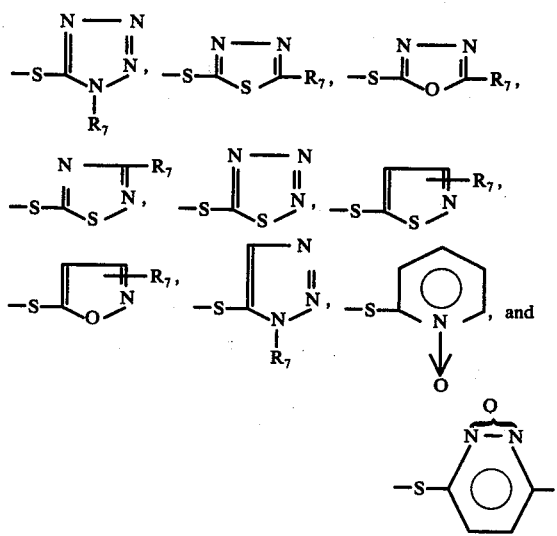

wherein $R_7$ is hydrogen or lower alkyl of 1 to 4 carbons (preferably methyl or ethyl) and $R_8$ is hydrogen, lower alkyl of 1 to 4 carbons (preferably methyl or ethyl), methoxy, hydroxy, or halogen (preferably chlorine).

The compounds of formula I wherein X is hydrogen, lower alkanoyloxy, or heterothio and $R_2$ is lower alkyl, phenyl, phenyl-lower alkyl or diphenyl-lower alkyl are prepared by reacting an α-amino intermediate of the formula

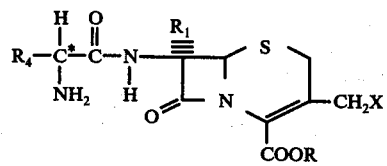

wherein X is hydrogen, lower alkanoyloxy, or heterothio, preferably in the form of its trifluoroacetic acid salt, with a compound of the formula

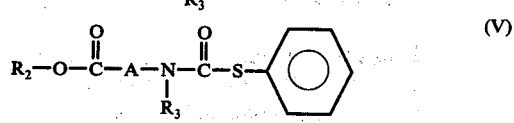

wherein $R_2$ is lower alkyl, phenyl, phenyl-lower alkyl or diphenyl-lower alkyl; $R_3$ is hydrogen or lower alkyl; A is as defined above; and halo is Cl or Br.

The intermediates of formulas II to V are prepared by known methods. For example, the compounds of formula II can be prepared by various methods including the acylation of a 7-amino cephalosporin of the formula

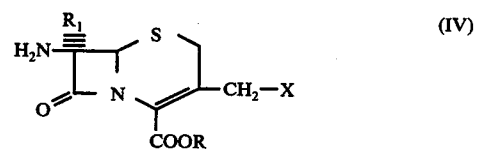

with a substituted α-amino acid of the formula

wherein Y is a protecting group such as

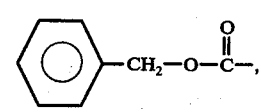

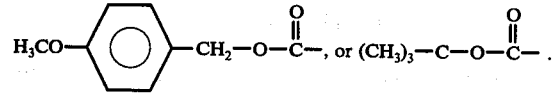

The α-amino protecting group is then removed by treating the resulting cephalosporin with trifluoroacetic acid and anisole. The desmethoxy α-amino compounds of formula II are taught in various U.S. patents as for example, 3,485,819; 3,507,861; 3,641,021; 3,796,801; 3,813,388; 3,821,207; etc. Similarly, the 7α-methoxy compounds of formula II prepared by various means are disclosed in U.S. patents as for example, 3,775,410; 3,780,031; 3,780,033; 3,780,034; 3,780,037; 3,887,549; etc. Also, the 7α-methoxy-7-amino compounds of formula VI are taught in U.S. Pat. No. 3,897,424.

The compounds of formula III can be prepared by reacting a compound of the formula

in the form of its hydrochloride salt with phosgene. The compound of formula VIII can be prepared by reacting the corresponding amino acid tosylate with the diazo compound of the formula

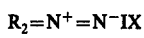

The compounds of formula I wherein X is hydrogen, lower alkanoyloxy, or heterothio and $R_2$ and R are hydrogen can be prepared by reacting a diphenylmethyl compound of the formula

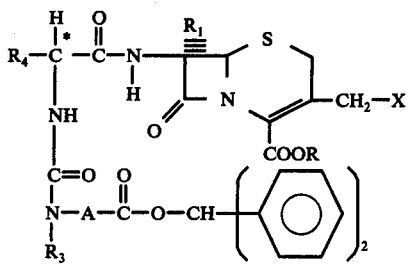

wherein R is hydrogen or diphenylmethyl with an acid, preferably trifluoroacetic acid, in the presence of anisole. The resulting acid compounds can then be treated with an alkali metal bicarbonate or alkaline earth metal bicarbonate to yield the compounds of formula I wherein $R_2$ and R are an alkali metal or alkaline earth metal ion.

The compounds of formula I wherein $R_1$ is either hydrogen or methoxy and X is pyridinium or carbamoyl substituted pyridinium are prepared by reacting the compound of the formula (or its sodium salt)

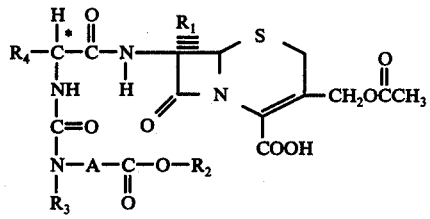

with pyridine or carbamoyl substituted pyridine in a polar solvent such as water and in the presence of a catalyst such as an alkali metal thiocyanate. U.S. Pat. No. 3,792,047 and German Offenlegungsschrift 2,234,280 both disclose methods for reacting a cephalosporin so as to replace an acetoxy group with a pyridinium group.

Also, the compounds of formula I wherein $R_1$ is either hydrogen or methoxy and X is heterothio can be prepared by reacting the compound of formula Ic with a mercaptan of the formula

or an alkali metal (preferably sodium) mercaptan salt of the formula

Methods for displacing the acetoxy group of a cephalosporin by a heterothio group are taught in various U.S. patents including 3,855,213; 3,890,309; 3,892,737; etc.

Alternatively, the compounds of formula I wherein X is hydrogen, lower alkanoyloxy, or heterothio can be prepared by reacting a compound of the formula

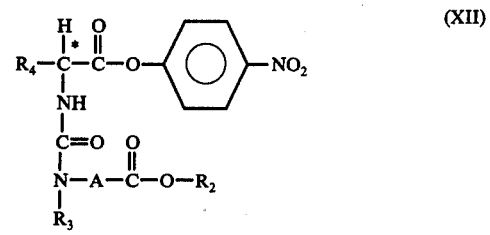

wherein $R_2$ is lower alkyl, phenyl, phenyl-lower alkyl, or diphenyl-lower alkyl, with an ester, preferably R is diphenylmethyl, of the compound of the formula VI.

The compound of formula XII can be prepared by reacting the isocyanatoacetic acid ester of the formula

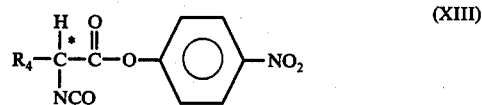

with an ester of the formula

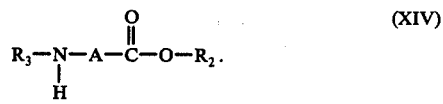

When $R_3$ is lower alkyl, the reaction is with the hydrochloride salt of the ester of formula XIV and is performed in the presence of triethylamine. The ester of formula XIV can be prepared by reacting the corresponding amino acid tosylate with the diazo compound of formula IX.

The compounds of formula I wherein R is lower alkyl, phenyl-lower alkyl, trihaloethyl, diphenyl-lower alkyl, or the acyloxymethyl group

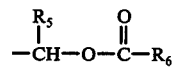

may be obtained by reacting the 7-amino cephalosporin of formula VI either before or after the acylation of the 7-amino substituent with one or two moles of a compound of the formula

wherein halo is preferably chlorine or bromine in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the cephalosporanic acid moiety either before or after the acylation reaction.

The carboxylate salts of the compound of formula I are formed by reacting the carboxyl group of the cephalosporanic acid moiety, i.e. R is hydrogen, with any of the salt forming ions described above.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention. Also, the second asymmetric carbon atom can be present in the alkylene chain, for example

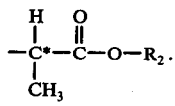

Preferred compounds of this invention are those wherein R is hydrogen or an alkali metal ion; X is pyridinium, carbamoyl substituted pyridinium (particularly where the carbamoyl group is in the 4-position), or heterothio; $R_4$ is cyclohexenyl, cyclohexadienyl, phenyl, benzyl, phenethyl, substituted phenyl, benzyl, or phenethyl wherein the substituent is on the phenyl ring and is one or two members selected from chloro, bromo, methyl, ethyl, methoxy, ethoxy and hydroxy, or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl, or ethyl; $R_2$ is hydrogen, straight or branched chain alkyl of 1 to 4 carbons, phenyl, benzyl, phenethyl, diphenylmethyl, or an alkali metal ion; A is straight or branched chain alkylene or 1 to 4 carbons; and $R_3$ is hydrogen or straight or branched chain alkyl of 1 to 4 carbons.

Also preferred as both final products and intermediates are the compounds of formula I wherein X is

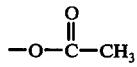

and A, R, $R_2$, $R_3$ and $R_4$ are as defined above.

The most preferred final compounds are those of formula I wherein R is hydrogen or an alkali metal ion; $R_4$ is 2-thienyl, 3-thienyl, phenyl, or 4-hydroxyphenyl; $R_2$ is hydrogen, straight or branched chain alkyl of 1 to 4 carbons, diphenylmethyl, or an alkali metal ion; A is straight or branched chain alkylene of 1 to 4 carbons; $R_3$ is hydrogen or methyl; and X is heterothio, particularly wherein X is

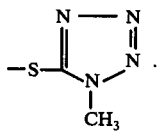

The compounds of formula I wherein R is hydrogen have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Enterobacter hafniae, Enterobacter cloacae, Klebsiella pneumoniae, Serratia marcescens*, etc. They may be used as antibacterial agents in a prophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg. of body weight, daily, orally or parenterally, in single or two to four divided doses to treat infections of bacterial origin, e.g., 5.0 mg./kg. in mice.

Up to about 600 mg. of a compound of formula I wherein R is hydrogen or a physiologically acceptable salt thereof may be incorporated in an oral dosage form such as tablets, capsules or elixirs or in an injectible form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight of such compounds admixed with, suspended or dissolved in conventional inert dry or aqueous carriers for application by washing or spraying.

They are also useful as nutritional supplements in animal feeds.

Illustrative process details are provided in the examples for the various reactions. All temperatures are on the centigrade scale.

EXAMPLE 1

7β-[[D-[[[(2-Ethoxy-2-oxoethyl)amino]carbonyl]-amino]-2-thienylacetyl]amino]-3-[[(1-methyl-1H-tetrazol-5-yl)thio]methyl]-8-oxo-5-thia-1-azabicyclo[4.2.0-]oct-2-ene-2-carboxylic acid a.

D-2-[[[(4-Methoxyphenyl)methoxy]carbonyl]amino]-2-thiopheneacetic acid 74 g. of D-2-Thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]-amino]-2-thiopheneacetic acid; m.p. 84°-94°; $[\alpha]_{20}^D$: −69° (c=1, tetrahydrofuran).

b.

7β-Amino-3-[[(1-methyl-1H-tetrazol-5-yl)thio]methyl]-8-oxo-5-thia-1-azabicyclo[4.2.0]oct-2-ene-2-carboxylic acid To a stirred suspension of 27.2 g. 7-amino cephalosporanic acid (0.1 mole) in 150 ml. of acetone and 100 ml. of H₂O at 0°-5° is added 50 ml. of 2N NaOH, with care being taken to keep the pH below 8.5. A solution of 12.7 g. (0.11 mole) of 1-methyl-5-mercapto-1H-tetrazole in 50 ml. of 2N NaOH is added, and the mixture is allowed to warm to room temperature. The stirred mixture is then maintained at 60° (internal temperature) under nitrogen for 3 hours at pH 7–7.5 by the periodic addition of dilute aqueous NaOH. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

c.
7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester A mixture of 16.4 g. (0.05 mole) of the acid product from part (b), 10.3 g. (0.054 mole) p-toluenesulfonic acid monohydrate, 350 ml. of dioxane (dried by passage through basic alumina), and dry CH₃OH is stirred at room temperature under nitrogen for 30 minutes. The clear solution is evaporated to a residue, and H₂O and CH₃OH are removed by four evaporations of 100 ml. quantities of dioxane. Fresh dioxane (300 ml.) is then added to the residue followed by a solution of crystalline diphenyldiazomethane (19.4 g., 0.10 mole) in 150 ml. of dry dimethoxyethane. The mixture is initially shaken vigorously for 10–15 minutes and then stirred at room temperature for 3 hours. Methanol (25 ml.) is added, and the red solution is stirred until it has turned yellow-orange. The solvents are removed in vacuo, and the residue is treated with 400 ml. of $CH_2Cl_2$ and a solution of 20 g. of $K_2HPO_4$ is 250 ml. of $H_2O$. The $CH_2Cl_2$ layer is washed with water and saturarted NaCl, and finally dried (MgSO₄) to give a residue after removal of the solvent in vacuo. Treatment of the residue with Et₂O gives a solid (27 g.). Column chromatography of this solid on silica gel by elution with CHCl₃ and then EtOAc-CHCl₃ (4:1) provides the desired product as a residue (12.9 g.). Treatment with EtOAc then provides 8.0 g. of the desired product as a pale yellow powder.

d.
7β-[[D-[[[(4-Methoxyphenyl)methoxy]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 46.2 g. of 7β-amino-3-[[(1-methyl-1H-tetrazol-5-yl)-thio]methyl]-8-oxo-5-thia-1-azabicyclo[4.2.0]oct-2-ene-2-carboxylic acid, dipheylmethyl ester from part (c) are dissolved in 550 ml. of anhydrous methylene chloride. 550 ml. of tetrahydrofuran and 36 g. of D-2-[[[(4-methoxyphenyl)-methoxy]carbonyl]amino]-2-thiopheneacetic acid, from part (a), are added. The reaction solution is cooled to 0° and a solution of 22.5 g. of dicyclohexylcarbodiimide in 150 ml. of anhydrous tetrahydrofuran is added dropwise over the course of 30 minutes. The mixture is then stirred for 90 minutes at 0° and finally 120 minutes at room temperature. The precipitated dicyclohexylurea (21 g.) is filtered off under suction and the filtrate is concentrated. The residue is taken up in a mixture of 1000 ml. of ethyl acetate and 400 ml. of tetrahydrofuran, filtered and the filtrate is washed first with sodium bicarbonate solution and then with water. This is then dried with magnesium sulfate, treated with activated carbon, filtered and the filtrate is then concentrated slowly under vacuum to a small volume. After standing overnight in the refrigerator, the precipitate crystals are filtered under suction to obtain 63.1 g. of 7β-[[D- [[[(4-methoxyphenyl)methoxyl]carbonyl]amino]-2-thienylacetyl]amino]-3-[[(1-methyl-1-H-tetrazol-5-yl)thiol]methyl]-8-oxo-5-thia-1-azabicyclo [4.2.0]oct-2-ene-2-carboxylic acid, diphenylmethyl ester; m.p. 130°–131° (dec.). $[\alpha]^D_{20}$: −117° (c=1, tetrahydrofuran).

e.
7β[D-2-Amino-2-(thienyl)acetamido]-3-[[(1-methyl-1H-tetrazol-5-yl) thio]methyl]-8-oxo-5-thia-1-azabicyclo[4.2.0]oct-2-ene-2-carboxylic acid, trifluoroacetic acid salt (1:1)

62 g. of the diphenylmethyl ester product from part (d) are added to 300 ml. of anisole with stirring. The mixture is cooled to 0° and 750 ml. of trifluoroacetic acid are added slowly. The mixture is stirred for 10 minutes at 0° and the anisole is evaporated at 0.1 mm. of Hg. and 35° bath temperature. The residue is treated with 250 ml. of petroleum ether, then 350 ml. of ether, stirred for one hour, and filtered with suction to yield 46.4 g. of 7β-[D-2-amino-2-(2-thienyl)acetamido]-3-[[(1-methyl-1H-tetrazol-5-yl)thio]-methyl]-8-oxo-5-thia-1-azabicyclo[4.2.0]oct-2-ene-2-carboxylic acid, trifluoroacetic acid salt (1:1); m.p. 138°–139° (dec.).

f.
7β-[[[[[(2-Ethoxy-2-oxoethyl)amino]carbonyl]amino]-2-thienylacetyl]amino]-3-[[(1-methyl-1-H-tetrazol-5-yl)thio]methyl]-8-oxo-5-thia-1-azabicyclo [4.2.0]oct-2-ene-2-carboxylic acid 1.60 g. (0.003 mole) of the trifluoroacetic acid salt product of part (e) are suspended in 35 ml. of methylene chloride and brought into solution by the addition of 0.73 ml. of triethylamine. To the resulting clear solution at 0°–5° is added dropwise, slowly, a solution of 0.516 g. of isocyanatoacetic acid ethyl ester in 13 ml. of methylene chloride and the mixture is then stirred for 3 hours more at room temperature. This mixture is then concentrated, taken up in water, shaken with ethyl acetate, the phases are separated, the aqueous phase is layered over with fresh ethyl acetate and then adjusted to pH 1.5 with 2N hydrochloric acid while cooling with ice. The phases are separated, the aqueous phase is again shaken twice with ethyl acetate. After drying with magnesium sulfate, filtering and concentrating the ethyl acetate solution, 1.3 g. of crude product is obtained. This product is reprecipitated from tetrahydrofuran-petroleum ether to yield 7β-[[D-[[[(2-ethoxy-2-oxoethyl)-amino]-carbonyl]amino]-2-thienylacetyl]amino]-3-[[(1-methyl-1H-tetrazol-5-yl) thiol]methyl]-8-oxo-5-thia-1-azabicyclo [4.2.0]-oct-2-ene-2-carboxylic acid, m.p. 115°–130° (dec.).

An aqueous equimolar solution of this acid and sodium bicarbonate is lyophilized to yield 7β-[[D-[[[(2-ethoxy-2-oxoethyl)    amino]carbonyl]amino]-2-thienylacetyl]amino]-3-[[(1-methy;-1H-tetrazol-5-yl) thiol]methyl]-8-    oxo-5-thia-1-azabicyclo[4.2.0.]pct-2-ene-2-carboxylic acid, sodium salt; m.p. 186°–187° (dec.). By substituting potassium bicarbonate for the sodium bicarbonate, one obtains the corresponding potassium salt.

EXAMPLE 2

7β-[[L-[[[(2-Ethoxy-2-oxoethyl)amino]carbonyl]-amino]-2-thienyl-acetyl]amino]-3-[[(1-methyl-1H-tetrazol-5-yl) thio]methyl]-8-oxo-5-tia-1-azabicyclo [4.2.0]pct-2-ene-2-carboxylic acid a.
L-2-[[[(4-Methoxyphenyl)methoxy)]carbonyl]carbonyl]amino]-2-thiopheneacetic acid L-2-Thienylglycine and p-methoxybenzyloxycarbonylazide are reacted according to the procedure of example 1 (a) to yield L-2-[[[(4-methoxyphenyl)methoxy]carbonyl]amino]-2-thiopheneacetic acid; m.p. 97°–98°[α]$_D^{25}$: +68° (c=1, tetrahydrofuran).

b. 7β[[L-[[[(4-Methoxyphenyl)methoxy]carbonyl]amino]-2-thienylacetyl]amino]-3-[[(1-methyl-1H-tetrazol-5-yl)-thio]methyl]-8-oxo-5-thia-1-azabicyclo [4.2.0]oct-2-ene-2-carboxylic acid, diphenylmethyl ester 4.6 g. of L-2-[[[(4-methoxyphenyl)methoxy]carbonyl]-amino]-2-thiopheneacetic acid from part (a) and 5.9 g. of 7β-amino-3-[[(1-methyl-1H-tetrazol-5-yl)thio]-methyl]-8-oxo-5-thia-1-azabicyclo [4.2.0]oct-2-ene-2-carboxylic acid, diphenylmethyl ester from example 1 (c) are reacted according to the procedure of example 1 (d) to yield 8.4 g. of 7β-[[L-[[[(4-methoxyphenyl)methoxy]carbonyl]amino]-2-thienyl-acetyl]amino]-3-[[(1-methyl-1H-tetrazol-5-yl) thiol]methyl]-8-oxo-5-thia-1-azabicyclo [4.2.0]oct-2-ene-2-carboxylic acid, diphenylmethyl ester which after concentration and treating with ether is obtained in amorphorus form.

c. 7β[L-2-Amino-2-(2-thienyl) acetamido]-3-[[(1-methyl-1H-tetrazol-5-yl) thiol]methyl]-8-oxo-5-thia-1-azabicyclo[4.2.0]oct-2-ene-2-carboxylic acid, trifluoroacetic acid salt (1:1)

1.6 g. of the diphenylmethyl ester product from part (b) are treated with trifluoroacetic acid and anisole according to the procedure of example 1 (e) to yield 1.1 g of 7β-[L-2-amino-2-(2thienyl) acetamido]-3-[[(1-methyl-1H-tetrazol-5-yl)-thio]methyl]-8-oxo-5-thia-1-azabicyclo [4.2.0]oct-2-ene-2-carboxylic acid, trifluoroacetic acid salt (1:1); m.p. 127°–131° (dec.).

d. 7β-[[L-[[[(2-Ethoxy-2-oxoethyl) amino]carbonyl]amino]-2-thienylacetyl]amino]-3-[[(1-methyl-1H-tetrazol-5-yl) thiol-methyl]-8-oxo-5-thia-1-azabicyclo [4.2.0]oct-2-ene-2-carboxylic acid 2.9 g. (0.005 mole) of the trifluoroacetic acid salt product from part (c) is reacted with isocyanatoacetic acid ethyl ester according to the procedure of example 1 (f) to yield 7β-[[L- [[[(2-ethoxy-2-oxoethyl)amino]-]amino]-2-thienylacetyl]amino-3-[[(1-methyl-1H-tetrazol-5-yl) thio]methyl]-8-oxo-5-thia-1-azabicyclo [4.2.0]oct-2-ene-2-carboxylic acid.

An aqueous equimolar solution of this acid and sodium bicarbonate is lyophilized to yield 7β-[[L-[[[(2-ethoxy-2-oxoethyl) amino]carbonyl]amino]-2-thienylacetyl]-amino]-3-[[(1-methyl-1H-tetrazol-5-yl) thio]methyl]-8-oxo-5-thia-1-azabicyclo [4.2.0]oct-2-ene-2-carboxylic acid, sodium salt. Similary, by substituting potassium bicarbonate for the sodium bicarbonate, one obtains the corresponding potassium salt.

EXAMPLE 3

7β[[D-[[[[2-(Diphenylmethoxy)-2-oxoethyl]amino]carbonyl]amino]-2-thienylacetyl]amino9 -3-[[(1-methyl-1-H-tetrazol-5-yl) thio]-methyl]-8-oxo-5-thia-1-azabicyclo [4.2.0]oct-2-ene-2-carboxylic acid a. Isocyanatoacetic acid, diphenylmethyl ester A suspension of 20 g. of glycine diphenylmethyl ester hydrochloride (prepared by reacting glycine tosylate and diphenyldiazomethane in dioxane followed by conversion to the hydrochloride salt) in 300 ml. of toluene is heated to boiling with stirring. At the boiling temperature, a strong stream of phosgene is passed through the suspension for three hours. The isocyanatoacetic acid, diphenylmethyl ester is then isolated by distillation; b.p.$_{0.01}$ 160°–170°.

b. 7β-[[D-[[[[2-(Diphenylmethoxy)-2-oxoethyl]amino]carbonyl]-amino]-2-thienylacetyl]amino]-3-[[(1-methyl1H-tetrazol-5-yl) thio]-methyl]-8-oxo-5-thia-1-azabicyclo [4.2.0]oct-2-ene- 2-carboxylic acid.

1.6 g. of the trifluoroacetic acid product from example 1(e) and the isocyanantoacetic acid, diphenylmethyl ester from part (a) are reacted according to the procedure of example 1(f) to yield 1.8 g of 7β-[[D-[[[[2-diphenylmethoxy)-2-oxoethyl]-amino]carbonyl]amino]-2-thienylacetyl]amino]-3-[[(1-methyl-1H-tetrazol-5-yl) thiol]methyl]-8-oxo-5-thia-1-azabicyclo [4.2.0]oct-2-ene-2-carboxylic acid; m.p. 75°–80° (dec.).

EXAMPLE 4

7β-[[D- [[[(Carboxymethyl) amino]carbonyl]amino]-2-thienylacetyl]-amino]-3-[[(1-methyl-1H-tetrazol-5-yl) thio]methyl]-8-oxo-5-thia-1-azabicyclo [4.2.0]oct-2-ene-2-carboxylic acid 1.6 g. of the product from example 3 is treated with 32 ml. of trifluoroacetic acid and 9.6 ml. of anisole according to the procedure of example 1 (e) to yield 1.1 g. of 7β-[[D-[[[(carboxymethyl) amino]carbonyl]amino]-2-thienylacetyl]-amino]-3-[[(1-methyl-1H-tetrazol-5-yl) thio]methyl]-8-oxo-5-thia-1-azabicyclo [4.2.0]oct-2-ene-2-carboxylic acid; m.p. 149°–157° (dec.).

An aqueous solution of this acid and two equivalents of sodium bicarbonate is lyophilized to yield 7β-[[D-[[[(carboxymethyl) amino]carbonyl]amino]-2-thienylacetylamino]-3-[[(1-methyl-1H-tetrazol-5-yl) thio]methyl]-8-oxo-5-thia-1-azabicyclo[4.2.0]oct-2-ene-2-carboxylic acid, disodium salt; m.p. 207°–212° (dec.). In an analogous manner one can obtain the dipotassium salt.

EXAMPLE 5

7β-[[L-[[[[2-(Diphenylmethoxy)-2-oxoethyl]amino]carbonyl]amino]-2-thienylacetyl]amino]-3-[[(1-methyl-1H-tetraol-5-yl) thiol]-methyl]-8-oxo-5-thia-1-azabicyclo [4.2.0]oct-2-ene-2-carboxylic acid The trifluoroacetic acid salt product from example 2(c) and the isocyanatoacetic acid, diphenylmethyl ester from example 3(a) are reacted according to the procedure of example 1(f) to yield 7β-[[L- [[[[2-(diphenylmethoxy)-2-oxoethyl]-amino]carbonyl]amino]-2-thienylacetyl]amino]-3-[[(1-methyl-1H-tetrazol-5-yl) thio]methyl]-8-oxo-5-thia-1-azabicyclo[4.2.0]oct2-ene-2-carboxylic acid.

EXAMPLE 6

7β-[[L-[[[(Carboxymethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid The product from example 5 is treated with trifluoroacetic acid and anisole according to the procedure of example 1(e) to yield 7β-[[L-[[[(carboxymethyl)amino]-carbonyl]amino]-2-thienylacetyl]amino]-3-[[(1-methyl-1H-tetrazol-5-yl)thiol]-methyl]-8-oxo-5-thia-1-azabicyclo[4.2.0]oct-2-ene-2-carboxylic acid.

An aqueous solution of this acid and two equivalents of sodium bicarbonate is lyophilized to yield 7β-[[L-[[[-(carboxymethyl)amino]carbonyl]amino]-2- thienylacetyl]amino]-3-[[(1-methyl-1H-tetrazol-5-yl)thio]methyl]-8-oxo-5-thia-1-azabicyclo[4.2.0]oct-2-ene-2-carboxylic acid, disodium salt. In an analogous manner one can obtain the dipotassium salt.

EXAMPLE 7

7α-Methoxy-7β-[[D,L-[[[[2-(diphenylmethoxy)-2-oxoethyl]amino]-carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid a.

7α-Methoxy-7β-[[D,L-[[[(4-methoxyphenyl)methoxy]-carbonyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 2.41 g. (.0075 mole) of D,L-2-[[[(4-methoxyphenyl)-methoxy]carbonyl]amino]-2-thiopheneactic acid (prepared according to the procedure of example 1(a)) is dissolved in an ice bath to 0°-5°, and 0.969 g. (0.0075 mole) of diisopropylethylamine and isobutylchloroformate are added to the cold solution. After 10 minutes, 3.28 g. (.00625 mole) of 7β-amino-7α-methoxy-3-[[(1-methyl-1H-tetrazol-5yl)thio]methyl]-8-oxo-5-thia-1-azabicyclo[4.2.0]oct-2-ene-2-carboxylic acid, diphenylmethyl ester is added to the reaction mixture and the ice bath is removed. Following three hours of stirring at room temprature, a second portion of mixed anhydride is prepared in a separate flask using the procedure described above. This solution is added to the reaction mixture and after 4.5 hours another batch of mixed anhydride prepared using half the quantities set forth above is added to the main reaction mixture. Stirring is continued at room temperature for 12 hours and the reaction mixture is then diluted with methylene chloride and washed with water, saturated aqueous sodium bicarbonate solution, and water. The organic layer is dried over sodium sulfate and the solvent is removed in vacuo to yield a foam. This crude product is chromatorgraphed on silica gel (200 g., 60-200 mesh) and the desired product is eluted with 9:1 and 4:1 methylene chloride:ethyl acetate. The oily product is precipitated as a powder from a methylene chloride-ether mixture and dried over phosphorous pentoxide in vacuo to yield 3.81 g. of 7α-methoxy-7β-[[D,L-[[[(4-methoxyphenyl)-methoxy]carbonyl]amino]-2-thienylacetyl]amino]-3-[[(1-methyl-1H-tetrazol-5-yl)thio]methyl]-8-oxo-5-thia-1-azabicyclo-[4.2.0]oct-2-ene-2-carboxylic acid, diphenylmethyl ester. Alternatively, the titled compound can be obtained by the following procedure.

129 mg. (0.4 mmole) of D,L-2-[[[(4-methoxyphenyl)-methoxy]carbonyl]amino]-2-thiopheneacetic acid is dissolved in 2 ml. of anhydrous methylene chloride and 47 mg. (0.2 mmole) of dicyclohexylcarbodiimide is added. The mixture is stirred for 15 minutes at room temperature during which time colorless dicyclohexylurea crystallizes. The suspension is directly filtered into a stirring solution of 77 mg. (0.147 mmole) of 7β-amino-7α-methoxy-3-[[(1-methyl-1H-tetrazol-5-yl)thio]methyl]-8-oxo-5-thia-1-azabicyclo[4.2.0]-oct-2 2-ene-2-carboxylic acid, diphenylmethyl ester in 1 ml. of methylene chloride. After stirring at room temperature for 19 hours, the mixture is diluted with methylene chloride, washed with pH 7.4 buffer, and dried over sodium sulfate. Removal of solvent under reduced pressure yields a crude oil which is chromatrographed on preparative thin layer chromatography silica gel plates developed in a 4:1 chloroform:ethyl acetate mixture. The desired product (58 mg.) is isolated as an oil.

b.

7α-Methoxy-7β-[D,L-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

The diphenylmethyl ester product from part (a) is reacted with trifluoroacetic acid in the presence of anisole according to the procedure of example 1(e) to yield the titled compound.

c.

7α-Methoxy-7β-[[D,-[[[[2-(diphenylmethyoxy)-2-oxoethyl]amino]-carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid The trifluoroacetic acid salt product of part (b) is suspended in methylene chloride and triethylamine and reacted with isocyanatoacetic acid diphenylmethyl ester according to the procedure of example 1(f) to yield 7α-methoxy-7β-[[D,L-[[[[2-(diphenylmethoxy)-2-oxoethyl]amino]carbonyl]amino]-2-thienylacetyl]-amino]-3-[[(1-methy-1H-tetrazol-5-yl) thio]methyl]-8-oxo-5-thia-1-azabicyclo[4.2.0]oct-2-ene-2-carboxylic acid.

EXAMPLE 8

7α-Methoxy-7β-[[D,,L-[[[(carboxymethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid The product from example 7 is treated with trifluoroacetic acid and anisole according to the procedure of example 1(e) to yield 7α-methoxy-7β-[[D,L-[[[(carboxymethyl)amino]carbonyl]-amino]-2-thienylacetyl]-amino]-3-[[(1-methyl-1H-tetrazol-5-yl)-thio]methyl]-8-oxo-5-thia-1-azabicyclo[4.2.0]oct-2-ene-2-carboxylic acid.

An aqueous solution of this acid and two equivalents of sodium bicarbonate is lyophilized to yield 7α-methoxy-7β-[[D,L-[[[(carboxymethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, disodium salt. In an analogous manner one can obtain the dipotassium salt.

EXAMPLES 9-38

Following the procedure of example 1 but employing the acylating agent shown in Col. I and the 7β-amino-7α-methoxy or desmethoxy-cephalosporanic acid ester shown in Col. II, one obtains the protected ester shown in Col. III. The protecting group and ester group are removed as the compound of Col. III is converted to its trifluoroacetic acid salt shown in Col. IV. The trifluoroacetic acid salt is reacted with the isocyanatoacetic acid ester of Col. V to yield the cephalosporanic compound shown in Col. VI. The compound of Col. VI can be reacted so as to reintroduce the ester group and yield the compound of Col. VII or can be treated according to known procedures to yield the corresponding salt.

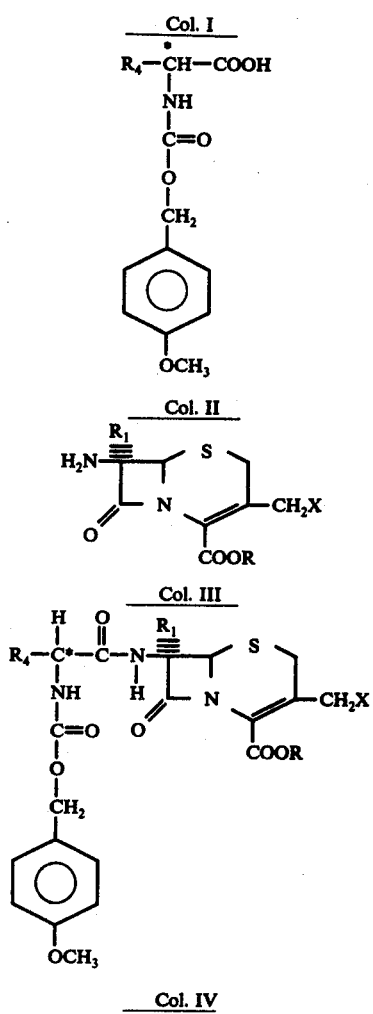

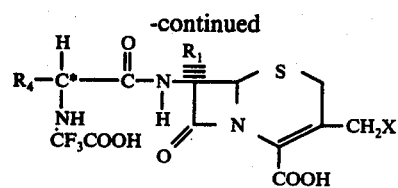

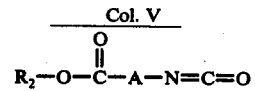

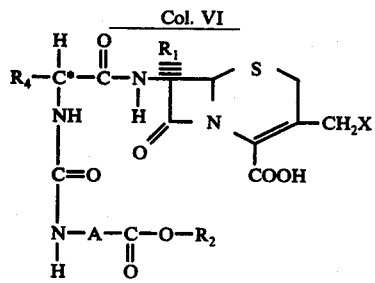

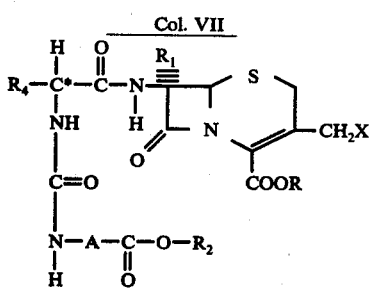

Alternatively, the α-aminocephalosporanic acid ester of Col. VIII can be treated with compound of Col. V to yield the ester of Co. VII. This ester can then be treated to remove the ester group and yield the cephalosporanic acid of Col. VI.

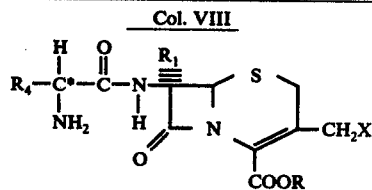

| Ex. | R₄ | A | R₂ | R₁ | R | X |
|---|---|---|---|---|---|---|
| 9 | thienyl | $-(CH_2)_2-$ | $-CH_3$ | $-H$ | $-CH_2-$phenyl | 1-methyl-tetrazol-5-ylthio |
| 10 | 5-chloro-2-thienyl | $-CH(CH_3)-$ | $-C_2H_5$ | $-OCH_3$ | $-CH(phenyl)_2$ | 1-methyl-tetrazol-5-ylthio |
| 11 | 4-methyl-2-thienyl | $-(CH_2)_4-$ | phenyl | $-H$ | $t-C_4H_9$ | 5-methyl-1,3,4-thiadiazol-2-ylthio |
| 12 | 2-thienyl | $-CH_2-$ | phenyl | $-H$ | $-CH(phenyl)_2$ | $-O-CO-C_2H_5$ |

-continued

Col. VIII

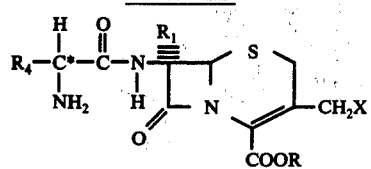

| Ex. | $R_4$ | A | $R_2$ | $R_1$ | R | X |
|---|---|---|---|---|---|---|
| 13 | furan | $-CH_2-$ | $-CH_2-C_6H_5$ | $-H$ | $-C_2H_5$ | $-O-CO-CH_3$ |
| 14 | furan | $-CH(CH_3)-CH_2-$ | $-C_2H_5$ | $-OCH_3$ | $-CH_2-C_6H_5$ | $-S-$(1-ethyl-tetrazol-5-yl) |
| 15 | 2-chlorofuran | $-(CH_2)_6-$ | $-C_2H_5$ | $-H$ | $-CH(C_6H_5)_2$ | $-S-$(5-methyl-1,3,4-thiadiazol-2-yl) |
| 16 | pyridine | $-CH_2-CH(CH_3)-CH_2-$ | $-CH_2-C_6H_5$ | $-OCH_3$ | $t-C_4H_9$ | $-S-$(1H-tetrazol-5-yl) |
| 17 | 2-chloro-4-methylpyridine | $-CH_2-$ | $-(CH_2)_2-C_6H_5$ | $-H$ | $-CH_2-C_6H_5$ | $-S-$(5-methyl-1,3,4-oxadiazol-2-yl) |
| 18 | thiophene | $-CH_2-$ | $-CH(C_6H_5)_2$ | $-H$ | $-CH(C_6H_5)_2$ | $-S-$(1-methyl-tetrazol-5-yl) |
| 19 | thiophene | $-CH(CH_3)-CH_2-$ | $-CH(C_6H_5)_2$ | $-OCH_3$ | $-CH(C_6H_5)_2$ | $-S-$(1-methyl-tetrazol-5-yl) |
| 20 | phenyl | $-CH_2-$ | $-C_2H_5$ | $-H$ | $-CH_2-C_6H_5$ | $-S-$(4-methyl-thiazol-2-yl) |
| 21 | phenyl | $-(CH_2)_2-$ | $-C_3H_7$ | $-OCH_3$ | $-CH(C_6H_5)_2$ | $-S-$(1,3,4-thiadiazol-2-yl) |
| 22 | phenyl | $-C(CH_3)_2-CH_2-$ | $-C_2H_5$ | $-H$ | $-CH_2-C_6H_5$ | $-O-CO-CH_3$ |
| 23 | 4-hydroxyphenyl | $-CH(CH_3)-$ | $-C_6H_5$ | $-OCH_3$ | $-CH(C_6H_5)_2$ | $-O-CO-CH_3$ |
| 24 | phenyl | $-CH(CH_3)-$ | $-CH(C_6H_5)_2$ | $-H$ | $-CH(C_6H_5)_2$ | $-S-$(1-methyl-tetrazol-5-yl) |
| 25 | benzyl | $-CH_2-$ | $-CH(C_6H_5)_2$ | $-OCH_3$ | $-CH(C_6H_5)_2$ | $-S-$(1-methyl-tetrazol-5-yl) |

-continued

Col. VIII

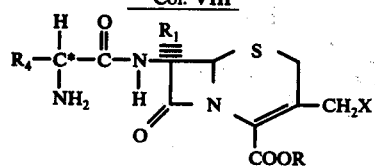

| Ex. | R₄ | A | R₂ | R₁ | R | X |
|---|---|---|---|---|---|---|
| 26 | HO-C₆H₄- | -(CH₂)₃- | -CH(C₆H₅)₂ | -H | -CH(C₆H₅)₂ | -S-(1-methyl-tetrazol-5-yl) |
| 27 | 3,4-Cl₂-C₆H₃- | -(CH₂)₅- | -C₂H₅ | -H | t-C₄H₉ | -S-(4-methyl-thiazol-2-yl) |
| 28 | H₃CO-C₆H₄-CH₂- | -CH₂- | -C₆H₅ | -OCH₃ | -CH₂CCl₃ | -S-(4-methyl-isoxazol-3-yl) |
| 29 | H₃C-C₆H₄- | -CH₂-CH(CH₃)- | -t-C₄H₉ | -H | -CH(C₆H₅)₂ | -S-(1-methyl-tetrazol-5-yl) |
| 30 | 2-thienyl | -CH(CH₃)-CH₂- | -i-C₃H₇ | -OCH₃ | -CH(CH₃)-O-C(O)CH₃ | -S-(5-methyl-1,3,4-thiadiazol-2-yl) |
| 31 | C₆H₅- | -CH₂- | -C₂H₅ | -H | Si(CH₃)₃ | -S-(5-methyl-1,3,4-oxadiazol-2-yl) |
| 32 | cyclohexyl | -C(CH₃)₂-CH₂- | -C₂H₅ | -H | -CH₂-C₆H₅ | -S-(1-methyl-tetrazol-5-yl) |
| 33 | cyclopropyl | -CH₂- | -CH₂-C₆H₅ | -OCH₃ | t-C₄H₉ | -S-(5-ethyl-1,3,4-thiadiazol-2-yl) |
| 34 | cyclohexyl | -(CH₂)₂- | -C₂H₅ | -H | -CH(C₆H₅)₂ | -S-(1H-tetrazol-5-yl) |
| 35 | C₆H₅- | -CH₂- | -C₂H₅ | -H | -CH(C₆H₅)₂ | -H |
| 36 | C₆H₅- | -CH₂- | -CH(C₆H₅)₂ | -OCH₃ | -CH(C₆H₅)₂ | -S-(1-methyl-tetrazol-5-yl) |
| 37 | -C₂H₅ | -CH₂- | -C₂H₅ | -H | t-C₄H₉ | -CH₃ |
| 38 | H- | -CH₂- | -CH₃ | -H | -CH₂CCl₃ | -S-(1,3,4-thiadiazol-2-yl), -O-C(O)-CH₃ |

The acylating agents shown in Col. I may be in either the D-, L-, or D,L-isomeric form.

Also, the compounds of Col. VI wherein R₂ is diphenylmethyl (i.e. examples 18, 19, 24–26 and 36) can be treated as in examples 4, 6 and 8 to yield the corresponding compounds wherein R₂ is hydrogen.

EXAMPLE 39

7β-[[D-[[[(Carboxymethyl)methylamino]carbonyl]-amino]-2-thienyl-acetyl]amino]-3-[[(1-methyl-1H-tetrazol-5-yl)thio]methyl]-8-oxo-5-thia-1-azabicyclo[4,2,0-]oct-2-ene-2-carboxylic acid a. D-2-[[[(4-Methoxyphenyl)methoxy]carbonyl]amino]-2-thiopheneacetic acid, 4-nitrophenyl ester 64.8 g. (0.2 mole) of D-2-[[[(4-methoxyphenyl)methoxy]-carbonyl]amino]-2-thiopheneacetic acid from example 1(a) are dissolved in 330 ml. of anhydrous tetrahydrofuran. A solution of 28 g. (0.2 mole) of 4-nitrophenol in 330 ml. of tetrahydrofuran is added. The mixture is cooled to 0° and a solution of 41.4 g. (0.2 mol) of dicyclohexylcarbodiimide in 134 ml. of tetrahydrofuran is added dropwise over a period of 90 minutes. The mixture is stirred overnight at 0°. It is then filtered and the filtrate is concentrated toyield 90 g. of crude product. Crystallization from toluene yields D-2-[[[(4-methoxyphenyl)-methoxy]carbonyl]amino]-2-thiopheneacetic acid, 4-nitrophenyl ester; m.p. 98°–105° (dec.).

b. D-2-Amino-2-thiopheneacetic acid, 4-nitrophenyl ester, hydrochloride 63.8 g. of D-2-[[[(4-methoxyphenyl)methoxy]carbonyl]-amino]-2thiopheneacetic acid, 4-nitrophenyl ester from part (a) are added at 0° to 300 ml. of a saturated solution of HCl gas in glacial acetic acid. The nitrophenyl ester from part (a) goes into solution and shortly thereafter the hydrochloride salt precipitates as a thick crystalline slurry. The hydrochloride salt is filtered under suction and additional hydrochloride salt is obtained from the filtrate by concentrating to give a combined yield of 46.2 g. of D-2-amino-2-thiopheneacetic acid, 4-nitrophenyl ester, hydrochloride; m.p. 173°–176° (dec.).

c. D-2-Isocyanato-2-thiopheneacetic acid, 4-nitrophenyl ester

Phosgene is passed into a boiling suspension of 21 g. of D-2-amino-2-thiopheneacetic acid, 4-nitrophenyl ester, hydrochloride in 300 ml. of toluene until a clear solution results. After concentrating, D-2-isocyanato-2-thiopheneacetic acid, 4-nitrophenyl ester remains as an oily residue.

d. D-2-[[[[2-(Diphenylmethoxy)-2-oxoethyl]methylamino]carbonyl]-amino]-2-thiopheneacetic acid, 4-nitrophenyl ester 4.4 g. (0.015 mole) of N-methylglycine, diphenylmthyl ester, hydrochloride (obtained by reacting N-methylglycine and diphenyldiazomethane followed by conversion to the hydrochloride salt) are suspended in 50 ml. of anhydrous tetrahydrofuran and 3.04 (0.01 mole) of D-2-isocyanato-2-thiopheneacetic acid, 4-nitrophenyl ester from part (c) are added. A solution of 1.01 g. (0.01 mole) of triethylamine are added to this suspension with stirring. This reaction mixture is stirred overnight, filtered, and the filtrate is concentrated. An oily residue solidifies on trituration with petroleum ether to yield 5 g. of D-2-[[[[2-(diphenylmethoxy)-2-oxoethyl]-methylamino]carbonyl]amino]-2-thiopheneacetic acid, 4-nitrophenyl ester as an amorphous powder; m.p. 60°–68°.

e. 7β-[[D-[[[[2-(Diphenylmethoxy)-2-oxoethyl]methylamino]-carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester 2.5 g. (0.005 mole) of 7β-amino-3-[[(1-methyl-1H-tetrazol-5-yl)thio]methyl]-8-oxo-5-thia-1-azabicyclo[4.2.0]-oct-2-ene-2-carboxylic acid, diphenylmethyl ester from example 1(c) are dissolved in 30 ml. of methylene chloride. 17 ml. of dimethylacetamide and 3.10 g. (0.0055 mole) of D-2-[[[[2-(diphenylmethoxy)-2-oxoethyl]methylamino]carbonyl]amino]-2-thiopheneacetic acid, 4-nitrophenyl ester from part (d) are added. The resulting mixture is stirred overnight at room temperature. Water is added and then the mixture is extracted with ethyl acetate. After concentrating and treating the residue with petroleum ether, 7β-[[D-[[[[2-(diphenylmethoxy)-2-oxoethyl]-methylamino]carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester; m.p. 105°–110°; is obtained as an amorphous powder.

f. 7β-[[D-[[[(Carboxymethyl)methylamino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid The diphenylmethyl ester product from part (e) is treated with trifluoroacetic acid and anisole according to the procedure of example 1(e) to yield 7β-[[D-[[[(carboxymethyl)methylamine]-carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid.

An aqueous solution of this acid and two equivalents of sodium bicarbonate is lyophilized to yield 7β-[[D-[[[(carboxymethyl)methylamino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, disodium salt; m.p. 190°–210°. In an analogous manner, one can obtain the dipotassium salt.

Similarly, by substituting L-2-[[[(4-methoxyphenyl)-methoxy]carbonyl]amino]-2-thiopheneacetic acid from example 2(a) for the D-isomer in part (a) and then following the procedure of example 39, one obtains 7β-[[L-[[[(carboxymethyl)-aminomethyl]carbonyl]amino]-2-thienylacetyl]amino]-3-[[(1-methyl-1H-tetrazol-5-yl)thio]methyl]-8-oxo-5-thia-1-azabicyclo-[4.2.0]oct-2-ene-2-carboxylic acid and its disodium and dipotassium salts.

EXAMPLE 40

7β-[[D,L-[[[(D,L-1-Carboxyethyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid a. D,L-Alanine, diphenylmethyl ester 9.0 g. of D,L-alanine and 19.0 g. of p-toluenesulfonic acid monohydrate are dissolved in 50 ml. of dimethylformamide. 21.1 g. of diphenyldiazomethane in 100 ml. of dimethylformamide are added dropwise at 50°. This mixture is stirred for 1 hour at 50° and then the solvent is distilled off in vacuum. The oily residue solidifies upon treatment with ether. The D,L-alanine, diphenylmethyl ester p-toluenesulfonate salt is recrystallized from acetonitrile and is obtained as white crystals, yield 13.5 g.; m.p. 170°–172°. 30 g. of this salt are dissolved in 200 ml. of water, layered over with 200 ml. of chloroform and 10 g. of sodium bicarbonate are added with frequent agitation. The organic phase is washed with 50 ml. of water, dried over sodium sulfate and evaporated. 17 g. of white crystalline D,L-alanine, diphenylmethyl ester are obtained, m.p. 60°–62°.

b. D,L-2-Isocyanato-2-thiopheneacetic acid, 4-nitrophenyl ester

Following the procedure of example 39(a), (b) and (c) but substituting D,L-2-[[[(4-methoxyphenyl)methoxy]-carbonyl]-amino]-2-thiopheneacetic acid for the D-isomer in part (a), one obtains, D,L-2-isocyanato-2-thiopheneacetic acid, 4-nitrophenyl ester as an oily residue.

c. D,L-2-[[[DL-2-(Diphenylmethoxy)-1-methyl-2-oxoethyl]amino]-carbonyl]amino]-2-thiopheneacetic acid, 4-nitrophenyl ester 6.09 g. of D,L-2-isocyanato-2-thiopheneacetic acid, 4-nitrophenyl ester from part (b) are dissolved in 20 ml. of tetrahydrofuran and added dropwise at 50° to a solution of 5.10 g. of D,L-alanine, diphenylmethyl ester, from part (a), in 50 ml. of tetrahydrofuran. This mixture is stirred for 30 minutes and the solvent is distilled off. The oily residue solidifies upon rubbing and is recrystallized from toluene to obtain 9.8 g. of white crystalline D,L-2-[[[D,L-2-(diphenylmethoxy)-1-methyl-2-oxoethyl]amino]carbonyl]amino]-2-thiopheneacetic acid, 4-nitrophenyl ester; m.p. 87°–90°.

d. 7β-[[D,L-[[[D,L-2-(Diphenylmethoxy)-1-methyl-2-oxoethyl]-amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 5.6 g. of D,L-2-[[[D,L-2-(diphenylmethoxy)-1-methyl-2-oxoethyl]amino]carbonyl]amino]-2-thiopheneacetic acid, 4-nitrophenyl ester from part (c) and 5 g. of 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester from example 1(c) and 1.35 g. of 1-hydroxybenzotriazole are stirred for 4 hours at 10° in 500 ml. of dimethylacetamide. The mixture is then poured into 400 ml. of water and extracted with ethyl acetate. The organic phase is extracted twice more with 50 ml. portions of 0.5 N sodium bicarbonate solution, dried and evaporated. The oily residue is dissolved in 20 ml. of tetrahydrofuran, treated with charcoal and stirred into a mixture of 100 ml. of ether and 100 ml. of petroleum ether to yield 7β-[[D,L-[[[D,L-2-(diphenylmethoxy)-1-methyl-2-oxoethyl]-amino]carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-carboxylic acid, diphenylmethyl ester; m.p. 93°–95°; as a beige powder.

e. 7β-[[D,L-[[[(D,L-1-Carboxyethyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid The diphenylmethyl ester product from part (d) is treated with trifluoroacetic acid and anisole (4:1) at 5° to yield as a beige powder 7β-[[D,L-[[[(D,L-1-carboxyethyl)-amino]carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid; m.p. 123°–127°.

An aqueous solution of this acid and two equivalents of sodium bicarbonate is lyophilized to yield 7β-[[D,L-[[[(D,L-carboxyethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, disodium salt. In an analogous manner, one can obtain the dipotassium salt.

EXAMPLE 41

7β-[[D-[[[(D,L-1-Carboxyethyl)amino]carbonyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid a. D-2-[[[[D,L-2-(Diphenylmethoxy)-1-methyl-2-oxoethyl]amino]-carbonyl]amino]-2-thiopheneacetic acid, 4-nitrophenyl ester D-2-isocyanato-2-thiopheneacetic acid, 4-nitrophenyl ester from example 39(c) and D,L-alanine diphenylmethyl ester from example 40(a) are reacted according to the procedure of example 40(c) to yield D-2-[[[[D,L-2-(diphenylmethoxy)-1-methyl-2-oxoethyl]amino]carbonyl]amino]-2-thiopheneacetic acid, 4-nitrophenyl ester; m.p. 141°–143°.

b. 7β-[[D-[[[[D,L-2-(Diphenylmethoxy)-1-methyl-2-oxoethyl]amino]-carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester The D-2-[[[[D,L-2-(diphenylmethoxy)-1-methyl-2-oxoethyl]-amino]carbonyl]amino]-2-thiopheneacetic acid, 4-nitrophenyl ester from part (a) and 7β-amino-3-[[(1-methyl-1H-tetrazol-5-yl)thio]-methyl]-8-oxo-5-thia-1-azabicyclo[4.2.0]oct-2-ene-2-carboxylic acid, diphenylmethyl ester from example 1(c) are reacted according to the procedure of example 40(d) to yield 7β-[[D-[[[D,L-2-(diphenylmethoxy)-1-methyl-2-oxoethyl]-amino]carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester; m.p. 128°–132°.

c. 7β-[[D-[[[(D,L-1-Carboxyethyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid The diphenylmethyl ester product from part (b) is treated with trifluoroacetic acid and anisole according to the procedure of example 40(e) to yield 7β-[[D-[[[(D,L-1-carboxyethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 150°–155°.

An aqueous solution of this acid and two equivalents of potassium bicarbonate is lyophilized to yield 7β-[[D-[[[(D,L-1-carboxyethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, dipotassium salt; m.p.

195°–199°. In a similar manner one obtains the corresponding disodium salt.

Similarly, by following the procedure of example 40 but substituting L-2-isocyanato-2-thiopheneacetic acid, 4-nitrophenyl ester for the D,L-isomeric mixture in part (c), one obtains 7β-[[L-[[(D,L-1-carboxyethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid and its dipotassium and disodium salts.

EXAMPLE 42

7β-[[D,L-[[[(1-Carboxy-1-methylethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid a. 2-Aminoisobutyric acid, diphenylmethyl ester 2-Aminosobutyric acid, p-toluenesulfonic acid monohydrate, and diphenyldiazomethane are reacted according to the procedure of example 40(a) to yield 2-aminoisobutyric acid, diphenylmethyl ester p-toluenesulfonic acid salt. Treatment with sodium bicarbonate yields 2-aminoisobutyric acid, diphenylmethyl ester; m.p. 74°–75°.

b.

D,L-2-[[[[2-(Diphenylmethoxy)-1,1-dimethyl-2-oxoethyl]amino]-carbonyl]amino]-2-thiopheneacetic acid, 4-nitrophenyl ester 6.09 g. of D,L-2-isocyanato-2-thiopheneacetic acid, 4-nitrophenyl ester from example 40(b) are dissolved in 30 ml. of tetrahydrofuran and a solution of 5.39 g. of 2-aminoisobutyric acid, diphenylmethyl ester in 50 ml. of tetrahydrofuran is added dropwise at 0°. After 40 minutes, the mixture is evaporated. Upon trituration of the residue with ether, crystallization of a yellow product occurs. Recrystallization from toluene yields 8.7 g. of white crystalline D,L-2-[[[[2-(diphenylmethoxy)-1,1-dimethyl-2-oxoethyl]amino]carbonyl]amino]-2-thiopheneacetic acid, 4-nitrophenyl ester; m.p. 161°–165°.

c.

7β-[[D,L-[[[2-(Diphenylmethoxy)-1,1-dimethyl-2-oxoethyl]-amino]carbonyl]amino]-2-thienylacetyl]amino]-3-[[(1-methyl-1H-tetrazol-5-yl)thio]methyl]-8-oxo-5-thia-1-azabicyclo-[4.2.0]oct-2-ene-2-carboxylic acid, diphenylmethyl ester The D,L-2-[[[[2-(diphenylmethoxy)-1,1-dimethyl-2-oxoethyl]amino]carbonyl]amino]-2-thiopheneacetic acid, 4-nitrophenyl ester from part (b) and 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester from example 1(c) are reacted according to the procedure of example 40(d) to yield 7β-[ [D,L-[[[2-(diphenylmethoxy)-1,1-dimethyl-2-oxoethyl]-amino]carbonyl]amino]-2-thiopheneacetyl]-amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester; m.p. 81°–86° (dec.).

d.

7β-[[D,L-[[[(1-Carboxy-1-methylethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid The diphenylmethyl ester product from part (c) is treated with trifluoroacetic acid and anisole (4:1) at 5° to yield 7β-[[D,L-[[[(1-carboxy-1-methylethyl)amino]-carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid.

An aqueous solution of this acid and two equivalents of sodium bicarbonate is lyophilized to yield 7β-[[D,L-[[[(1-carboxy-1-methylethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, disodium salt. In an analogous manner one can obtain the corresponding dipotassium salt.

EXAMPLE 43

7β-[[D-[[[(1Carboxy-1-methylethyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid a.

D-2-[[[[2-(Diphenylmethoxy)-1,1,-dimethyl-2-oxoethyl]amino]-carbonyl]amino]-2-thiopheneacetic acid, 4-nitrophenyl ester The D-2-isocyanato-2-thiopheneacetic acid, 4-nitrophenyl ester from example 39(c) and the 2-aminoisobutyric acid, diphenylmethyl ester from example 42(a) are reacted according to the procedure of example 42(b) to yield D-2-[[[[2-(diphenylmethoxy)-1,1-dimethyl-2-oxoethyl]amino]carbonyl]amino]-2-thiopheneacetic acid, 4-nitrophenyl ester; m.p. 162°–165°.

b.

7β-[[D-[[[2-(Diphenylmethoxy)-1,1-dimethyl-2-oxoethyl]amino]-carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester The D-2-[[[[2-(diphenylmethoxy)-1,1-dimethyl-2-oxoethyl]-amino]carbonyl]amino]-2-thiopheneacetic acid, 4-nitrophenyl ester from part (a) and 7β-amino-3-[[(1-methyl-1H-tetrazol-5-yl)-thio]methyl]-8-oxo-5-thia-1-azabicyclo[4.2.0]oct-2-ene-2-carboxylic acid, diphenylmethyl ester from example 1(c) are reacted according to the procedure of example 40(d) to yield 7β-[[ D-[[[2-(diphenylmethoxy)-1,1-dimethyl-2-oxoethyl]-amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, m.p. 113°–117°.

c.

7β-[[D-[[[(1Carboxy-1-methylethyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid The diphenylmethyl ester product from part (b) is treated with trifluoroacetic acid and anisole (4:1) at 5° to yield 7β-[[D-[[[(1-carboxy-1-methylethyl)amino]carbonyl]-amino]-2-thienylacetyl]amino]-3-[[(1-methyl-1H-tetrazol-5-yl)-thio]methyl]-8-oxo-5-thia-1-azabicyclo[4.2.0]oct-2-ene-2-carboxylic acid; m.p. 145°–149° (dec.).

An aqueous solution of this acid and two equivalents of potassium bicarbonate is lyophilized to yield 7β-[[D-[[[(1-carboxy-1-methylethyl)amino]carbonyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, dipotassium salt;

m.p. 137°–182° (dec.). In an analogous manner one can obtain the corresponding disodium salt.

Similarly, by following the procedure of example 42 but substituting L-2-isocyanato-2-thiopheneacetic acid, 4-nitrophenyl ester in part (b) for the D,L-isomeric mixture, one obtains 7β-[[L-[[[(1-carboxy-1-methylethyl)amino]carbonyl]-amino]-2-thienylacetyl]amino]-3-[[(1-methyl-1H-tetrazol-5-yl)-thio]methyl]-8-oxo-5-thia-1-azabicyclo[4.2.0]oct-2-ene-2-carboxylic acid and its dipotassium and disodium salts.

EXAMPLES 44–67

Following the procedure of examples 39 to 43 but employing the isocyanato, 4-nitrophenyl ester of Col. I and the amino acid ester of Col. II one obtains the acylating agent of Col. III. Reaction of the acylating agent of Col. III and the 7β-amino cephalosporin of Col. IV yields the cephalosporin product of Col. V.

Col. I: $R_4$–*CH(NCO)–C(=O)–O–C$_6$H$_4$–NO$_2$

Col. II: H–N(R$_3$)–A–C(=O)–O–R$_2$

Col. III: $R_4$–*CH(NH–C(=O)–N(R$_3$)–A–C(=O)–O–R$_2$)–C(=O)–O–C$_6$H$_4$–NO$_2$

Col. IV: 7β-amino cephalosporin with R$_1$, COOR, CH$_2$X substituents

Col. V: coupled cephalosporin product

| Ex | R$_4$ | R$_2$ | R$_3$ | A | R | R$_1$ | X |
|---|---|---|---|---|---|---|---|
| 44 | 2-thienyl | –CH(C$_6$H$_5$)$_2$ | –CH$_3$ | –CH$_2$– | –CH(C$_6$H$_5$)$_2$ | –OCH$_3$ | –S–(1-methyl-1H-tetrazol-5-yl) |
| 45 | 2-thienyl | –CH(C$_6$H$_5$)$_2$ | –H | –CH(CH$_3$)– | –CH(C$_6$H$_5$)$_2$ | –OCH$_3$ | –S–(1-methyl-1H-tetrazol-5-yl) |
| 46 | 2-thienyl | –C$_2$H$_5$ | –H | –(CH$_2$)$_2$– | –CH$_2$–C$_6$H$_5$ | –H | –S–(5-methyl-1,3,4-thiadiazol-2-yl) |
| 47 | 5-chloro-2-thienyl | –C$_6$H$_5$ | –C$_2$H$_5$ | –CH$_2$– | –t-C$_4$H$_9$ | –OCH$_3$ | –S–(1-methyl-1H-tetrazol-5-yl) |
| 48 | 2-furyl | –CH$_2$–C$_6$H$_5$ | –H | –(CH$_2$)$_3$– | –C$_2$H$_5$ | –OCH$_3$ | –S–(1,3,4-thiadiazol-2-yl) |
| 49 | 2-furyl | –CH$_3$ | –CH$_3$ | –CH(CH$_3$)–CH$_2$– | –CH(C$_6$H$_5$)$_2$ | –H | –S–(1,3,4-thiadiazol-2-yl) |

-continued

Col. I $$R_4-\overset{*}{C}H-\overset{O}{\overset{\|}{C}}-O-\underset{}{\phantom{}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!-NO_2$$
with NCO group Col. II $$H-N-A-\overset{O}{\overset{\|}{C}}-O-R_2$$
with $R_3$ on N Col. III $R_4-\overset{*}{C}H-C(=O)-O-C_6H_4-NO_2$ with NH–C(=O)–N(R_3)–A–C(=O)–O–R_2

Col. IV

Cephem nucleus with $H_2N$, $R_1$, S, CH_2X, COOR

Col. V

Full coupled structure

| Ex | R_4 | R_2 | R_3 | A | R | R_1 | X |
|---|---|---|---|---|---|---|---|
| 50 | 2-pyridyl | –CH(C_6H_5)_2 | –C_3H_7 | –CH_2– | –CH(C_6H_5)_2 | –H | –S-(1,3,4-oxadiazol-2-yl)-5-CH_3 |
| 51 | 2-Cl-5-pyridyl | –C_6H_5 | –H | –CH_2–CH(CH_3)–CH_2– | –H | –OCH_3 | –S-(1,3,4-thiadiazol-2-yl)-5-CH_3 |
| 52 | C_6H_5– | –CH(C_6H_5)_2 | –CH_3 | –CH_2– | –CH(C_6H_5)_2 | –H | –S-(1-methyltetrazol-5-yl) |
| 53 | C_6H_5– | –CH(C_6H_5)_2 | –CH_3 | –CH_2– | –CH(C_6H_5)_2 | –OCH_3 | –S-(1-methyltetrazol-5-yl) |
| 54 | C_6H_5– | –CH(C_6H_5)_2 | –H | –CH(CH_3)– | –CH(C_6H_5)_2 | –H | –S-(1-methyltetrazol-5-yl) |
| 55 | C_6H_5– | –CH(C_6H_5)_2 | –H | –CH(CH_3)– | –CH(C_6H_5)_2 | –OCH_3 | –S-(1-methyltetrazol-5-yl) |
| 56 | HO–C_6H_4– | –CH(C_6H_5)_2 | –CH_3 | –CH_2– | –CH(C_6H_5)_2 | –H | –S-(1-methyltetrazol-5-yl) |
| 57 | HO–C_6H_4– | –CH(C_6H_5)_2 | –H | –CH(CH_3)– | –CH(C_6H_5)_2 | –OCH_3 | –S-(1-methyltetrazol-5-yl) |

-continued

| Col. I | Col. II |
|---|---|
| 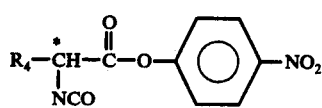 | 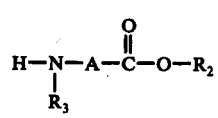 |

| Col. III | Col. IV |
|---|---|
| 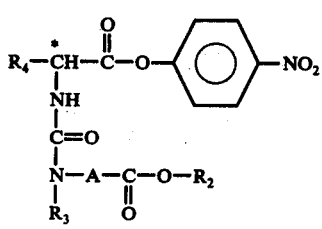 | 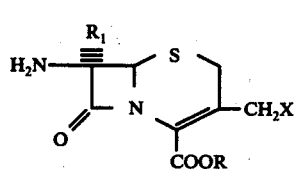 |

Col. V

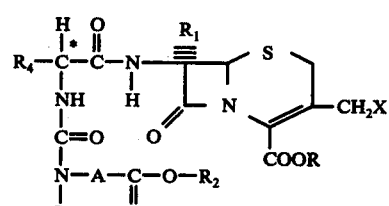

| Ex | R₄ | R₂ | R₃ | A | R | R₁ | X |
|---|---|---|---|---|---|---|---|
| 58 | 2,4-diCl-phenyl | -CH(C₆H₅)₂ | -H | -CH(CH₃)- | -CH(C₆H₅)₂ | -OCH₃ | -S-(triazole-NH) |
| 59 | C₆H₅-CH₂- | -CH₃ | -CH₃ | -CH(CH₃)- | -H | -H | -S-(4-methyl-isothiazole) |
| 60 | 4-CH₃-C₆H₄-CH₂- | -CH₂-C₆H₅ | -H | -CH₂- | -CH₂-O-C(O)-CH₃ | -H | -S-(3-methyl-isoxazole) |
| 61 | C₆H₅- | -CH₃ | -H | -(CH₂)₂- | t-C₄H₉ | -OCH₃ | -O-C(O)-CH₃ |
| 62 | C₆H₅- | -C₂H₅ | t-C₄H₉ | -(CH₂)₂- | t-C₄H₉ | -H | -O-C(O)-C₂H₅ |
| 63 | C₆H₅- | -CH(C₆H₅)₂ | -H | -CH₂- | -CH(C₆H₅)₂ | -OCH₃ | -S-(1-methyl-tetrazole) |
| 64 | C₆H₁₁- | -C₆H₅ | -CH₃ | -(CH₂)₅- | -CH(CH₃)-O-C(O)-CH₃ | -H | -S-(5-ethyl-thiadiazole) |
| 65 | C₆H₁₁- | -CH₂-C₆H₅ | -CH₃ | -C(CH₃)₂-CH₂- | -H | -H | -S-(1-methyl-tetrazole) |
| 66 | H- | -C₆H₅ | -H | -CH₂- | t-C₄H₉ | -H | -S-(5-methyl-oxadiazole) |
| 67 | C₂H₅- | -C₆H₅ | -H | -CH(CH₃)- | t-C₄H₉ | -OCH₃ | -S-(thiadiazole-H) |

The compounds of Col. V of examples 44, 45, 52 to 58 and 63 can be treated with trifluoroacetic acid and anis- The isocyanato, 4-nitrophenyl esters of Col. I of examples 44 to 67 may be in either the D-, the L-, or the D,L-isomeric form.

EXAMPLE 68

7β-[[D-[[[(Carboxymethyl)amino]carbonyl]amino]-2-thienylacetyl]amino-3-[[4-(aminocarbonyl)pyridino]methyl]-8-oxo-5-thia-1-azabicyclo[4.2.0]oct-2-ene-2-carboxylic acid, sodium salt a.

3-[(Acetyloxy)methyl-7β-[[D-[[[(4-methoxyphenyl)methoxy]carbonyl]amino]-2-thienylacetyl]amino]-8-oxo-5-thia-1-azabicyclo[4.2.0]oct-2-ene-2-carboxylic acid 3.2 g. (0.01 mole) of the D-2-[[[(4-methoxyphenyl)methoxy]carbonyl]amino]-2-thiopheneacetic acid from example 1(a) are brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 3.26 g. (0.1012 mol) of 7-aminocephalosporanic acid and 3.1 ml. of triethylamine in 40 ml. of methylene chloride. The mixture is stirred for 1 hour at −5° and 1 hour at 5°. This mixture is then evaporated to dryness in a rotary evaporator. The solid residue is triturated with ether and filtered under suction. The substance is then dissolved in ice water, layered over with ethyl acetate and acidified to pH 2.5. The layers are separated, the aqueous layer is extracted once more with ethyl acetate, the combined ethyl acetate extracts are washed with water, dried with magnesium sulfate and concentrated. The residue (4.9 g.) is dissolved in 200 ml. of ethyl acetate and the solution is treated with activated carbon. After filtration, 2 g. of 3-[(acetyloxy)methyl]-7β-[[D-[[[(4-methoxyphenyl)methoxy]carbonyl]amino]-2-thienylacetyl]amino]-8-oxo-5-thia-1-azabicyclo[4.2.0]-oct-2-ene-2-carboxylic acid, crystallize; m.p. 142°-143° (dec.).

b.

3-[(Acetyloxy)methyl]-7β-[D-2-amino-2-(2-thienyl)acetamido]-8-oxo-5-thia-1-azabicyclo[4.2.0]oct-2-ene-2-carboxylic acid, trifluoroacetic acid salt (1:1)

2.0 g. of the product from part (a) are added at −5° to a mixture of 10 ml. of trifluoroacetic acid and 4 ml. of anisole. The mixture is stirred for 10 minutes and is then concentrated in a rotary evaporator. The residue is treated with ether and filtered to yield the titled compound.

c.

3-[(Acetyloxy)methyl]-7β-[[D-[[[[2-(diphenylmethoxy)-2-oxoethyl]amino]carbonyl]amino]-2-thienylacetyl]-amino]-8-oxo-5-thia-1-azabicyclo[4.2.0]oct-2-ene-2-carboxylic acid the trifluoroacetic acid salt product from part (b) and the isocyanatoacetic acid, diphenylmethyl ester from example 3(a) are reacted according to the procedure of example 3(b) to yield the titled compound.

d.

3-[(Acetyloxy)methyl]-7β-[[D-[[[(carboxymethyl)amino]carbonyl]amino]-2-thienylacetyl]amino]-8-oxo-5-thia-1-azabicyclo[4.2.0]oct-2-ene-2-carboxylic acid, disodium salt The product from part (c) is treated with trifluoroacetic and anisole according to the procedure of example 1(e) to yield 3-[(acetyloxy)methyl]-7β-[[D-[[[(carboxymethyl)-amino]carbonyl]amino]-2-thienylacetyl]-amino]-8-oxo-5-thia-1-azabicyclo[4.2.0]oct-2-ene-2-carboxylic acid.

An aqueous solution of this acid and two equivalents of sodium bicarbonate is lyophilized to yield 3-[(acetyloxy)-methyl]-7β-[[D-[[[(carboxymethyl)amino]-carbonyl]amino]-2-thienyacetyl]amino]-8-oxo-5-thia-1-azabicyclo[4.2.0]oct-2-ene-2-carboxylic acid, disodium salt.

e.

7β-[[D-[[[(Carboxymethyl)amino]carbonyl]amino]-2-thienylacetyl]amino]-3-[[4-(aminocarbonyl)pyridino]-methyl]-8-oxo-5-thia-1-azabicyclo[4.2.0]oct-2-ene-2-carboxylic acid, sodium salt A mixture of 0.005 mole of the disodium salt product of part (d), 0.0075 mole of 4-pyridinecarboxamide, 12 g. of potassium thiocyanate and 7.5 ml. of water are heated at 50° for 24 hours. The clear solution is passed through a chromatography column filled with 150 g. of ion exchanger Amberlite XAD-2. The column is eluted with water and all fractions in which the desired product is shown by thin layer chromatography are combined. The combined fractions are lyophilized. The amorphous residue is triturated with ether and filtered under suction to yield 7β-[[D-[[[(carboxymethyl)amino]carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid, sodium salt.

Similarly, by employing the L-2-[[[(4-methoxyphenyl)-methoxy]carbonyl]amino]-2-thiopheneacetic acid from example 2(a) in place of the D-isomer in the above procedure, one obtains 7β-[[L-[[[(carboxymethyl)amino]carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid, sodium salt.

EXAMPLES 69–83

Following the procedure of example 68, but employing the cephalosporanic acid disodium salt of Col. I and the pyridine compound of Col. II, one obtains the product shown in Col. III.

| | Col. I | | | Col. II |
|---|---|---|---|---|
| | 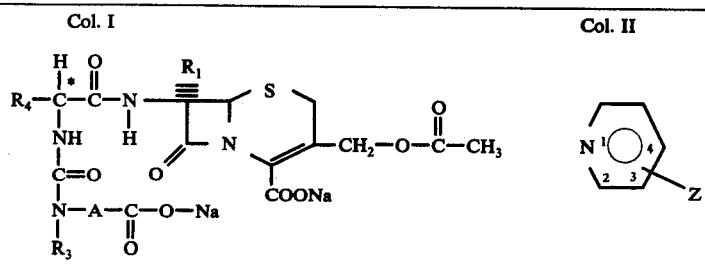 | | | |

Col. III

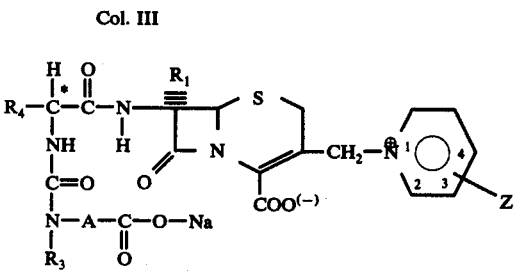

| Ex. | $R_4$ | $R_3$ | A | $R_1$ | Z |
|---|---|---|---|---|---|
| 69 | 2-thienyl | —H | —$CH_2$— | —$OCH_3$ | $-\overset{O}{\underset{}{C}}-NH_2$ (4) |
| 70 | 5-Cl-2-thienyl | —$CH_3$ | —$(CH_2)_2$— | —H | $-\overset{O}{\underset{}{C}}-NH_2$ (4) |
| 71 | 2-thienyl | —$C_2H_5$ | —CH—$CH_2$—<br>\|<br>$CH_3$ | —H | —H |
| 72 | 2-furyl | —H | —CH—$(CH_2)_2$—<br>\|<br>$CH_3$ | —$OCH_3$ | $-\overset{O}{\underset{}{C}}-NH_2$ (4) |
| 73 | 2-furyl | —H | —$(CH_2)_4$— | —H | $-\overset{O}{\underset{}{C}}-NH_2$ (2) |
| 74 | 2-pyridyl | —H | $CH_3$<br>\|<br>—C—$CH_2$—<br>\|<br>$CH_3$ | —H | —H |
| 75 | phenyl | —H | —$CH_2$— | —H | $-\overset{O}{\underset{}{C}}-NH_2$ (4) |
| 76 | 4-HO-phenyl | —H | —$CH_2$— | —$OCH_3$ | $-\overset{O}{\underset{}{C}}-NH_2$ (4) |
| 77 | phenyl | —$CH_3$ | —$CH_2$— | —H | $-\overset{O}{\underset{}{C}}-NH_2$ (4) |
| 78 | 4-HO-phenyl | —$CH_3$ | —CH—$CH_2$—<br>\|<br>$CH_3$ | —$OCH_3$ | $-\overset{O}{\underset{}{C}}-NH_2$ (4) |
| 79 | benzyl | —$C_2H_5$ | —$(CH_2)_3$— | —H | —H |
| 80 | 4-$H_3CO$-phenyl | —H | —$CH_2$— | —$OCH_3$ | $-\overset{O}{\underset{}{C}}-NH_2$ (3) |

-continued

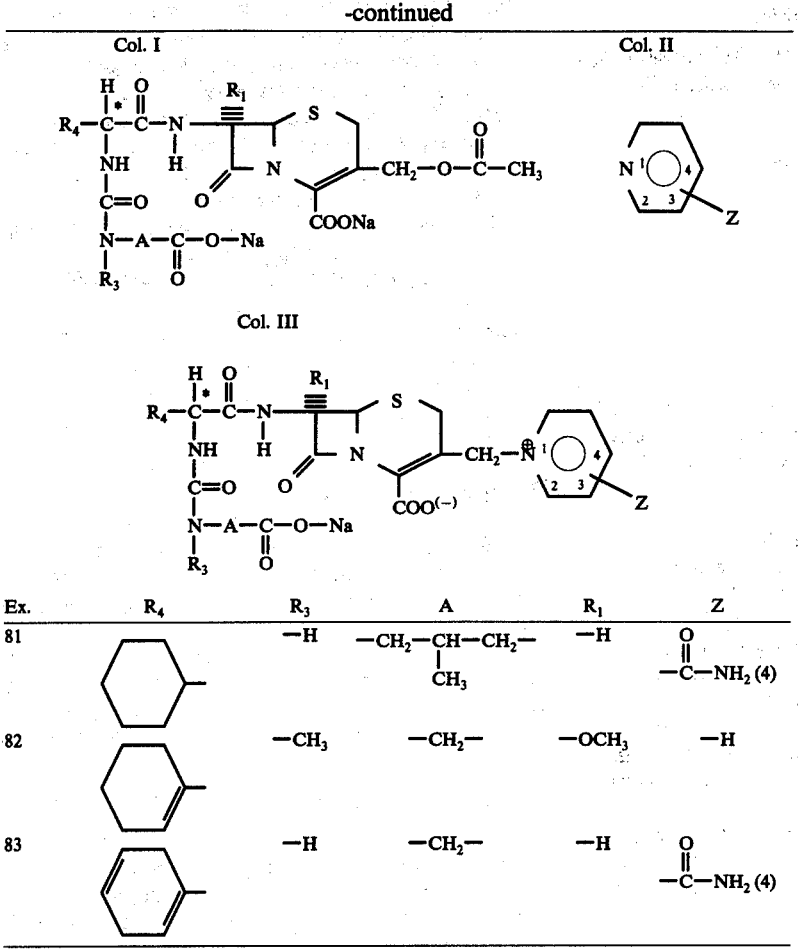

The disodium salts of Col. I may be in the D-, the L-, or the D,L-isomeric form.

EXAMPLE 84

7β-[[D-[[[(Carboxymethyl)amino]carbonyl]amino]-2-thienylacetyl]amino]-3-[[(1-oxo-2-pyridinyl)thio]methyl]-8-oxo-5-thia-1-azabicyclo[4.2.0]oct-2-ene-2-carboxylic acid 0.003 mole of 3-[(acetyloxy)methyl]-7β-[[D-[[[(carboxymethyl)amino]carbonyl]amino]-2-thienylacetyl]amino]-8-oxo-5-thia-1-azabicyclo[4.2.0]oct-2-ene-2-carboxylic acid, disodium salt from example 68(d) and 0.004 mole of 2-mercaptopyridine, 1-oxide sodium salt are dissolved in 15 ml. of water and heated overnight at 50°. The reaction mixture is then diluted with water, filtered, and the clear solution is adjusted to a pH of 2 by the addition of 2N hydrochloric acid. The resulting precipitate is filtered under suction to obtain 7β-[[D-[[[-(carboxymethyl)amino]carbonyl]amino]-2-thienylacetyl]amino]-3-[[(1-oxo-2-pyridinyl)-thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(carboxymethyl)amino]carbonyl]amino]-2-thienylacetyl]amino]-8-oxo-5-thia-1-azabicyclo-[4.2.0]oct-2-ene-2-carboxylic acid, disodium salt, one obtains the corresponding final product in the L-form.

Similarly, the various 3-[(acetyloxy)methyl]-7α-methoxy or desmethoxy-7β-acylureido-cephalosporanic acid disodium salts of Col. I of examples 69 to 83 may be employed in the procedure of example 84 to obtain other 3-[[(1-oxo-2-pyridinyl)thio]methyl]cephalosporins within the scope of the invention.

EXAMPLE 85

7β-[[D-[[[(Carboxymethyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid 3-[(Acetyloxy)methyl]-7β-[[D-[[[(carboxymethyl)amino]carbonyl]amino]-2-thienylacetyl]amino]-8-oxo-5-thia-1-azabicyclo[4.2.0]oct-2-ene-2-carboxylic acid, disodium salt from example 68(d) is dissolved in a mixture of acetone:water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yield 7β-[-[D-[[[(carboxymethyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(carboxymethyl)amino]carbonyl]amino]-2-thienylacetyl]amino]-8-oxo-5-thia-1-azabicyclo[4.2.0]oct-2-ene-2-carboxylic acid, disodium salt, one obtains the corresponding final product in the L- form.

EXAMPLES 86–94

Following the procedure of example 85 but substituting for the 1-oxopyridazine-3-thiol one of the following:

2-oxopyridazine-3-thiol
6-methyl-1-oxopyridine-3-thiol
6-methoxy-1-oxopyridazine-3-thiol
6-t-butyl-2-oxopyridazine-3-thiol
6-ethyl-2-oxopyridazine-3-thiol
6-hydroxy-1-oxopyridazine-3-thiol
6-hydroxy-2-oxopyridazine-3-thiol
6-chloro-1-oxopyridazine-3-thiol
6-chloro-2-oxopyridazine-3-thiol one obtains:

7β-[[D-[[[(carboxymethyl)amino]carbonyl]amino]-2-thienylacetyl]amino]-3-[[(2-oxopyridazin-3-yl)thio]methyl]-8-oxo-5-thia-1-azabicyclo[4.2.0]oct-2-ene-2-carboxylic acid, 7β-[[D-[[[(carboxymethyl)amino]carbonyl]amino]-2-thienylacetyl]amino]-3-[[(6-methyl-1-oxopyridazin-3-yl)thio]-methyl]-8-oxo-5-thia-1-azabicyclo[4.2.0]oct-2-ene-2-carboxylic acid, 7β-[[D-[[[(carboxymethyl)amino]carbonyl]amino]-2-thienylacetyl]amino]-3-[[(6-methoxy-1-oxopryidazin-3-yl)thio]-methyl]-8-oxo-5-thia-1-azabicyclo[4.2.0]oct-2-ene-2-carboxylic acid, 7β-[[D-[[[(carboxymethyl)amino]carbonyl]amino]-2-thienylacetyl]amino]-3-[[(6-t-butyl-2-oxopyridazin-3-yl)thio]-methyl]-8-oxo-5-thia-1-azabicyclo[4.2.0-]oct-2-ene-2-carboxylic acid, 7β-[[D-[[[(carboxymethyl)amino]carbonyl]amino]-2-thienylacetyl]amino]-3-[[(6-ethyl-2-oxopyridazin-3-yl)thio]-methyl]-8-oxo-5-thia-1-azabicyclo[4.2.0-]oct-2-ene-2-carboxylic acid, 7β-[[D-[[[(carboxymethyl)amino]carbonyl]amino]-2-thienylacetyl]amino]-3-[[(6-hydroxy-1-oxopyridazin-3-yl)thio]methyl]-8-oxo-5-thia-1-azabicyclo[4.2.0]oct-2-ene-2-carboxylic acid, 7β-[[D-[[[(carboxymethyl)amino]carbonyl]amino]-2-thienylacetyl]amino]-3-[[(6-hydroxy-2-oxopyridazin-3-yl)thio]methyl]-8-oxo-5-thia-1-azabicyclo[4.2.0]oct-2-ene-2-carboxylic acid, 7β-[[[(carboxymethyl)amino]carbonyl]amino]-2-thienyl-acetyl]amino]-3-[[(6-chloro-1-oxopyridazin-3-yl)thio]methyl]-8-oxo-5-thia-1-azabicyclo[4.2.0-]oct-2-ene-2-carboxylic acid, and 7β-[[D-[[[(carboxymethyl)amino]carbonyl]-amino]-2-thienylacetyl]amino]-3-[[(6-chloro-2-oxopyridazin-3-yl)thio]methyl]-8-oxo-5-thia-1-azabicyclo[4.2.0]oct-2-ene-2-carboxylic acid, respectively.

Similarly, by employing 3-[(acetyloxy)methyl]-7β-[[L-[[[(carboxymethyl)amino]carbonyl]amino]-2-thienylacetyl]amino-8-oxo-5-thia-1-azabicyclo[4.2.0-]oct-2-ene-2-carboxylic acid, disodium salt in place of the D-isomer in examples 85 to 94, the corresponding final products in the L-iosmer form are obtained. Additionally, the various 3-[(acetyloxy)methyl]7α-methoxy or desmethoxy-7β-acylureido-cephalosporanic acid disodium salts shown in Col. I of examples 69 to 83 may be employed in the procedure of examples 85 to 94 to obtain other compounds with the scope of the invention.

EXAMPLES 95–105

Following the procedure of example 85 but employing the 3-[(acetyloxy)methyl]-7α-methoxy or desmethoxy-7-acylureido cephalosporin disodium salt of Col. I an the heteromercapto of Col. II, one obtains the 3-heterothio compounds of Col. III.

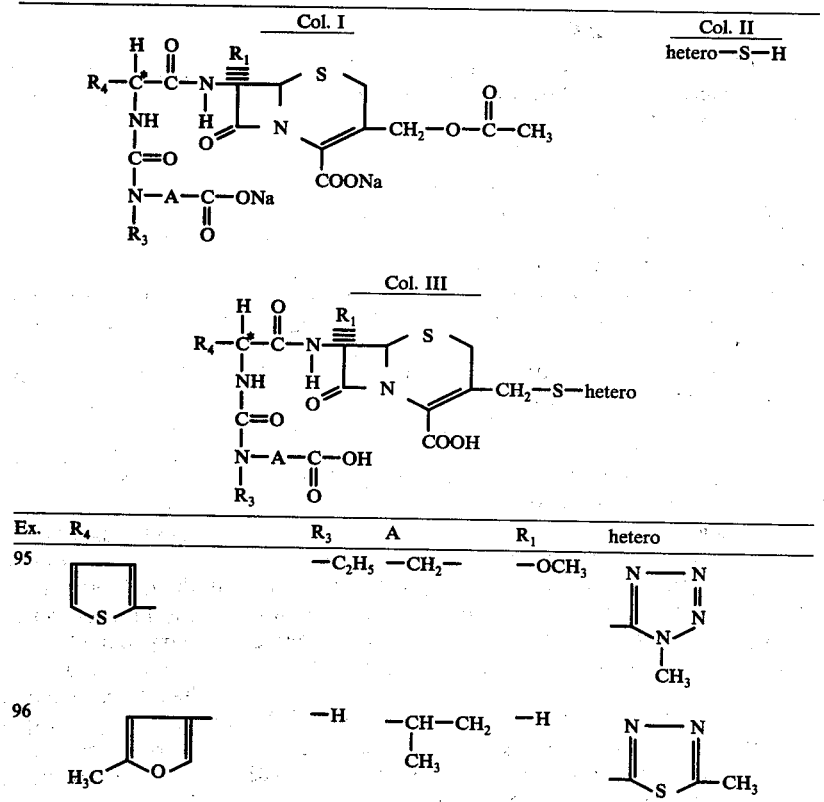

| Ex. | R₄ | R₃ | A | R₁ | hetero |
|-----|----|----|----|----|--------|
| 95 | (thiophene) | —C₂H₅ | —CH₂— | —OCH₃ | (N—N=N—N with N-CH₃ tetrazole) |
| 96 | (methylfuran, H₃C–O) | —H | —CH—CH₂ with CH₃ | —H | (N—N thiadiazole with S, CH₃) |

-continued

| # | (col A) | (col B) | (col C) | (col D) | (col E) |
|---|---|---|---|---|---|
| 97 | pyridyl | —CH₃ | —(CH₂)₃— | —H | thiadiazole-CH₃ |
| 98 | phenyl | —H | —C(CH₃)₂— | —OCH₃ | N-methyl tetrazole |
| 99 | Cl-phenyl-CH₂— | t-C₄H₉ | —(CH₂)₂— | —H | triazole-H |
| 100 | HO-phenyl | —C₂H₅ | —CH₂— | —OCH₃ | thiadiazole |
| 101 | phenyl-(CH₂)₂— | —H | —(CH₂)₄— | —H | isothiazole-CH₃ |
| 102 | cyclohexenyl | —CH₃ | —CH(C₂H₅)—CH₂— | —OCH₃ | isoxazole-C₂H₅ |
| 103 | cyclohexenyl | —H | —CH(CH₃)—CH₂— | —H | N-ethyl tetrazole |
| 104 | cyclopentyl | —H | —CH₂— | —H | thiadiazole-H |
| 105 | C₂H₅— | —H | —CH₂— | —OCH₃ | oxadiazole-CH₃ |

The disodium salt compounds of Col. I can be in the D—, the L—, or the D,L-isomeric form.

What is claimed is:
1. A compound of the formula

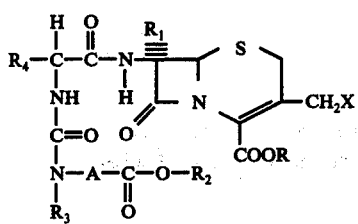

wherein R is hydrogen, lower alkyl, phenyl-lower alkyl, diphenyl-lower alkyl, tri(lower alkyl)silyl, trihaloethyl, an alkali metal ion, an alkaline earth metal ion, dibenzylamine, N,N-dibenzylethylendiamine, methylamine, triethylamine, N-ethylpiperidine, or

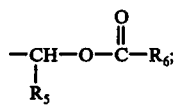

$R_1$ is in the α-configuration and is hydrogen or methoxy; $R_2$ is hydrogen, lower alkyl, phenyl, phenyl-lower alkyl, diphenyl-lower alkyl, an alkali metal ion, or an alkaline earth metal ion; $R_3$ is hydrogen or lower alkyl; A is straight or branched chain alkylene of 1 to 6 carbons; $R_4$ is phenyl, phenyl-lower alkyl, substituted phenyl or phenyl-lower alkyl wherein said phenyl substituent is one or two members selected from the group consisting of halogen, lower alkyl of 1 to 4 carbons, lower alkoxy of 1 to 4 carbons, and hydroxy, or a mono substituted or unsubstituted heterocyclic selected from the group consisting of 2-thienyl, 3-thienyl, 2-furyl, and 3-furyl wherein said heterocyclic substituent is attached at an available carbon atom and is halogen or lower alkyl of 1 to 4 carbons; $R_5$ is hydrogen or lower alkyl; $R_6$ is lower alkyl; and X is heterothio selected from the group consisting of

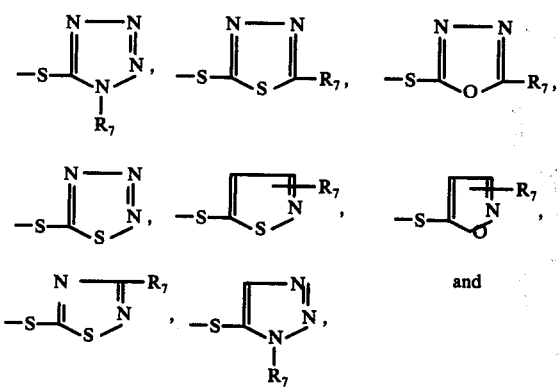

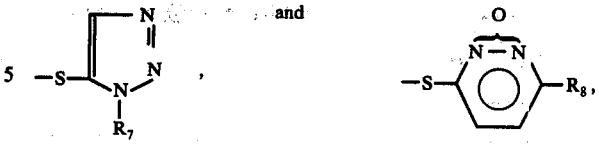

wherein $R_7$ is hydrogen, methyl or ethyl and $R_8$ is hydrogen, methyl, ethyl, methoxy, hydroxy, or chlorine.

3. The compound of claim 2 wherein R is hydrogen, diphenylmethyl, sodium or potassium; $R_4$ is 2-thienyl, 3-thienyl, phenyl, or 4-hydroxyphenyl; and $R_2$ is hydrogen, straight or branched chain alkyl of 1 to 4 carbons, diphenylmethyl, sodium, or potassium.

4. The compound of claim 3 wherein X is

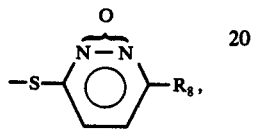

wherein $R_7$ is hydrogen or lower alkyl of 1 to 4 carbons and $R_8$ is hydrogen, lower alkyl of 1 to 4 carbons, methoxy, hydroxy, or halogen.

2. The compound of claim 1 wherein R is hydrogen, straight or branched chain alkyl of 1 to 4 carbons, benzyl, phenethyl, diphenylmethyl, trimethylsilyl, 2,2,2-trichloroethyl, an alkali metal ion, an alkaline earth metal ion, dibenzylamine, N,N-dibenzylethylenediamine, methylamine, triethylamine, N-ethylpiperidine, or

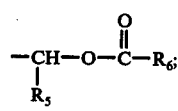

$R_2$ is hydrogen, lower alkyl of 1 to 4 carbons, phenyl, benzyl, phenethyl, diphenylmethyl, an alkali metal ion, or an alkaline earth metal ion; $R_3$ is hydrogen, lower alkyl of 1 to 4 carbons; A is straight or branched chain alkylene of 1 to 4 carbons; $R_4$ is phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a mono substituted or unsubstituted heterocylic selected from the group consisting of 2-thienyl, 3-thienyl, 2-furyl, and 3-furyl wherein said heterocyclic substituent is attached at an available carbon atom and is chloro, bromo, methyl, or ethyl; $R_5$ is hydrogen or straight or branched chain alkyl of 1 to 4 carbons; $R_6$ is straight or branched chain alkyl of 1 to 4 carbons; and X is heterothio selected from the group consisting of and $R_7$ is hydrogen, methyl, or ethyl.

5. The compound of claim 3 wherein X is

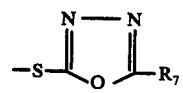

and $R_7$ is hydrogen, methyl, or ethyl.

6. The compound of claim 3 wherein X is

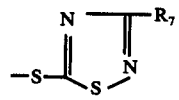

and $R_7$ is hydrogen, methyl, or ethyl.

7. The compound of claim 3 wherein X is

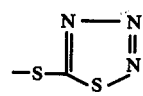

8. The compound of claim 3 wherein X is

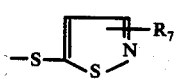

and $R_7$ is hydrogen, methyl, or ethyl.

9. The compound of claim 3 wherein X is

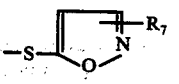

and $R_7$ is hydrogen, methyl, or ethyl.

10. The compound of claim 3 wherein X is

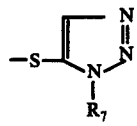

and R₇ is hydrogen, methyl, or ethyl.

11. The compound of claim 3 wherein X is

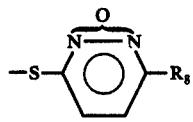

and R$_8$ is hydrogen, methyl, ethyl, methoxy, hydroxy, or chlorine.

12. The compound of claim 3 wherein X is

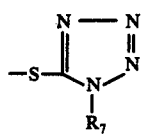

and R₇ is hydrogen, methyl, or ethyl.

13. The compound of claim 12 wherein R₇ is methyl.

14. The compound of claim 13 wherein R₁ is methoxy and R₄ is 2-thienyl.

15. The compound of claim 13 wherein R₁ is hydrogen and R₄ is 2-thienyl.

16. The compound of claim 15 wherein R is hydrogen, sodium, or potassium; R₂ is -C₂H₅; A is —CH₂—; and R₃ is —H.

17. The compound of claim 16, 7β-[[D-[[[(2-ethoxy-2-oxoethyl)amino]carbonyl]amino]-2-thienylacetyl]-amino]-3-[[(1-methyl-1H-tetrazol-5-yl)thio]methyl]-8-oxo-5-thia-1-azabicyclo-[4.2.0]oct-2-ene-2-carboxylic acid.

18. The compound of claim 15 wherein R is hydrogen; R₂ is diphenylmethyl; R₃ is —H; and A is —CH₂—.

19. The compound of claim 18, 7β-[[D-[[[2-(diphenyl-methoxy)-2-oxoethyl]amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid.

20. The compound of claim 15 wherein R and R₂ are the same and are both hydrogen, sodium or potassium; R₃ is —H; and A is —CH₂—.

21. The compound of claim 20, 7β-[[D-[[[(carboxymethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid.

22. The compound of claim 15 wherein R and R₂ are both diphenylmethyl; R₃ is —CH₃; and A is —CH₂—.

23. The compound of claim 15 wherein R and R₂ are the same and are both hydrogen, sodium or potassium; R₃ is —CH₃; and A is —CH₂—.

24. The compound of claim 15 wherein R and R₂ are both diphenylmethyl; R₃ is —H; and A is

25. The compound of claim 15 wherein R and R₂ are both the same and are hydrogen, sodium, or potassium; R₃ is —H; and A is

26. The compound of claim 25, 7β-[[D,L-[[[(D,L-1-carboxyethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid.

27. The compound of claim 25, 7β-[[D-[[[(D,L-1-carboxyethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid.

28. The compound of claim 15 wherein R and R₂ are diphenylmethyl; R₃ is —H; and A is

29. The compound of claim 15 wherein R and R₂ are both the same and are hydrogen, sodium or potassium; R₃ is —H; and A is

30. The compound of claim 29, 7β-[[D,L-[[[(1-carboxy-1-methylethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid.

31. The compound of claim 29, 7β-[[D-[[[(1-carboxy-1-methylethyl)amino]carbonyl]amino]-2-thienylacetyl]-amino]-3-[[(1-methyl-1H-tetrazol-5-yl)thio]methyl]-8-oxo-5-thia1-azabicyclo[4.2.0]oct-2-ene-2-carboxylic acid.

32. The compound of claim 23, 7β-[[D-[[[(carboxymethyl)-methylamino]carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid.

* * * * *

UNITED STATES PATENT AND TRADEMARK OFFICE
CERTIFICATE OF CORRECTION

PATENT NO. : 4,097,670
DATED : June 27, 1978
INVENTOR(S) : Hermann Breuer et al.

It is certified that error appears in the above-identified patent and that said Letters Patent are hereby corrected as shown below:

Col. 1, line 34, change "alkyl()silyl," to -- alkyl)silyl --.

Col. 3, line 24, add -- alkyl -- as follows:

and remove "alkyl" from the beginning of line 26.

Col. 5, line 6, "$R_2=N^+=N^-$ IX" should read as follows:

Col. 10, line 21, "7β-[[[[(2-" should read -- 7β-[[D-[[[(2 --.

Col. 10, line 52, "[4.2.0]pct-" should read --[4.2.0]oct- --.

Col. 10, line 61, "-5-tia-" should read -- -5-thia- --.

Col. 10, Line 62, "[4.2.0]pct-" should read -- [4.2.0]oct- --.

Col. 14, line 28 "3-[[(1-methy-1H" should read -- 3-[[(1-methyl-1H --.

Col. 14, line 33, "[[D,,L-" should read -- [[D,L- --.

Col. 20, Example 37 under heading X the structure should read:

UNITED STATES PATENT AND TRADEMARK OFFICE
CERTIFICATE OF CORRECTION

PATENT NO. : 4,097,670
DATED : June 27, 1978
INVENTOR(S) : Hermann Breuer et al.

It is certified that error appears in the above-identified patent and that said Letters Patent are hereby corrected as shown below:

Col. 21, line 5 "[4,2,0]" should read -- [4.2.0] --.

Col. 21, line 19, "toyield" should read -- to yield --.

Col. 21, line 54, "diphenylmt-" should read --diphenylmet--.

Col. 22, line 34, "methylamine" should read -- methylamino--.

Col. 23, line 63, take out the hyphen after "thio]".

Col. 24, line 1, take out the hyphen after"yethyl)".

Col. 24, line 3, take out the hyphen after "[4.2.0]".

Col. 31 after the Example 67, add the following after "anis-"

-- ole according to the procedure of example 1(e) to yield the compounds wherein R and $R_2$ are hydrogen. --.

UNITED STATES PATENT AND TRADEMARK OFFICE
CERTIFICATE OF CORRECTION

PATENT NO. : 4,097,670
DATED : June 27, 1978          Page 3 of 3
INVENTOR(S) : Hermann Breuer et al.

It is certified that error appears in the above-identified patent and that said Letters Patent are hereby corrected as shown below:

In the claims, under claim one (1), the sixth structure should read as follows:

In Claim two (2) at the end of line 65 of column 43 insert

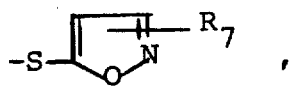   ,

Signed and Sealed this

Ninth Day of January 1979

[SEAL]

Attest:

RUTH C. MASON
Attesting Officer

DONALD W. BANNER
Commissioner of Patents and Trademarks